United States Patent
Azuma et al.

(10) Patent No.: US 11,448,631 B2
(45) Date of Patent: Sep. 20, 2022

(54) PLANT MONITORING APPARATUS, PLANT MONITORING METHOD, AND COMPUTER-READABLE RECORDING MEDIUM

(71) Applicant: NEC CORPORATION, Tokyo (JP)

(72) Inventors: Tan Azuma, Tokyo (JP); Yusuke Kikuchi, Tokyo (JP); Kousuke Ishida, Tokyo (JP); Shunsuke Akimoto, Tokyo (JP); Kenichiro Fujiyama, Tokyo (JP); Shinji Oominato, Tokyo (JP)

(73) Assignee: NEC CORPORATION, Tokyo (JP)

( * ) Notice: Subject to any disclaimer, the term of this patent is extended or adjusted under 35 U.S.C. 154(b) by 223 days.

(21) Appl. No.: 16/817,816

(22) Filed: Mar. 13, 2020

(65) Prior Publication Data
US 2020/0292514 A1    Sep. 17, 2020

(30) Foreign Application Priority Data
Mar. 14, 2019   (JP) .............................. JP2019-046895

(51) Int. Cl.
*G01N 33/00*   (2006.01)
*A01G 24/00*   (2018.01)
(Continued)

(52) U.S. Cl.
CPC ......... *G01N 33/0098* (2013.01); *A01G 24/00* (2018.02); *G01N 29/12* (2013.01); *G01N 29/4436* (2013.01)

(58) Field of Classification Search
CPC .. G01N 29/069; G01N 33/24; G01N 33/0098; G01N 29/12; G01N 29/4436;
(Continued)

(56) References Cited

U.S. PATENT DOCUMENTS

| 6,536,553 B1 * | 3/2003 | Scanlon | G01N 29/069 |
| | | | 181/108 |
| 2004/0095154 A1 | 5/2004 | Lundstorm et al. | |

(Continued)

FOREIGN PATENT DOCUMENTS

| JP | 51-52613 A | 5/1976 |
| JP | 05-505674 A | 8/1993 |

(Continued)

OTHER PUBLICATIONS

Communication dated Aug. 12, 2020, from the European Patent Office in European Application No. 20162934.2.

(Continued)

*Primary Examiner* — Catherine T. Rastovski
*Assistant Examiner* — Kaleria Knox
(74) *Attorney, Agent, or Firm* — Sughrue Mion, PLLC

(57) ABSTRACT

A plant monitoring apparatus 100 includes: a soil state estimation unit 200 that estimates a state of soil by, with use of frequency association information calculated based on vibration measured via the soil, referencing soil state estimation information in which the frequency association information and information indicating states of the soil are associated with soil states; and a plant state estimation unit 300 that estimates a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface.

15 Claims, 24 Drawing Sheets

(51) Int. Cl.
*G01N 29/12* (2006.01)
*G01N 29/44* (2006.01)

(58) Field of Classification Search
CPC ......... G01G 3/16; A01G 24/00; A63F 13/245; G01S 19/13
See application file for complete search history.

(56) References Cited

U.S. PATENT DOCUMENTS

| 2015/0081058 A1* | 3/2015 | Oliver | A63F 13/245 |
| | | | 700/91 |
| 2016/0270289 A1* | 9/2016 | Schildroth | G01S 19/13 |

FOREIGN PATENT DOCUMENTS

| JP | 2015-112083 A | 6/2015 | | |
| JP | 2015-202056 A | 11/2015 | | |
| JP | 2017-072383 A | 4/2017 | | |
| WO | 2016/136213 A1 | 9/2016 | | |
| WO | WO-2016136213 A1 * | 9/2016 | ............... | E02D 1/02 |
| WO | 2019/031181 A1 | 2/2019 | | |
| WO | WO-2019031181 A1 * | 2/2019 | ............... | A01G 7/00 |

OTHER PUBLICATIONS

Communication dated Apr. 14, 2020, from the Japanese Patent Office in Application No. 2019-046895.

* cited by examiner

Fig. 4

| SOIL LAYER | TRANSMISSION TIME | START INFORMATION | END INFORMATION |
|---|---|---|---|
| 1 | T1 | a1 | b1 |
| 2 | T2 | a2 | b2 |
| 3 | T3 | a3 | b3 |
| ⋮ | ⋮ | ⋮ | ⋮ |

41

| SOIL LAYER | TRANSMISSION TIME | SELECTED TIME |
|---|---|---|
| 1 | T1 | Td1 |
| 2 | T2 | Td2 |
| 3 | T3 | Td3 |
| ⋮ | ⋮ | ⋮ |

| RESONANCE FREQUENCY [Hz] | HARDNESS [kg/m²] | ROOT QUANTITY [m/m³] | MOISTURE CONTENT [%] | SOIL COMPOSITION |
|---|---|---|---|---|
| 10 | 1000 | 1.0 | 10 | Clay |
| 20 | 2000 | | | |
| ⋮ | ⋮ | | | |
| ⋮ | ⋮ | 2.0 | | |
| ⋮ | ⋮ | ⋮ | | |
| ⋮ | ⋮ | ⋮ | | |
| ⋮ | ⋮ | ⋮ | 20 | |
| ⋮ | ⋮ | ⋮ | ⋮ | |
| ⋮ | ⋮ | ⋮ | ⋮ | Silt |
| ⋮ | ⋮ | ⋮ | ⋮ | Sand |
| ⋮ | ⋮ | ⋮ | ⋮ | ⋮ |

| PORTION | CHANGE PARAMETER | | CHANGE INFORMATION | | | | | | |
|---|---|---|---|---|---|---|---|---|---|
| | | | fc1 CHANGE | fc1 Q FACTOR CHANGE | fc2 CHANGE | fc2 Q FACTOR CHANGE | fc3 CHANGE | fc3 Q FACTOR CHANGE | ... |
| STEM | DIAMETER | +10.0[mm] | +0.1[Hz] | 0 | 0 | 0 | 0 | 0 | ... |
| | | ... | ... | ... | ... | ... | ... | ... | ... |
| | HEIGHT | +10.0[mm] | 0 | 0 | 0 | 0 | +0.3[Hz] | 0 | ... |
| | | ... | ... | ... | ... | ... | ... | ... | ... |
| | INCLINATION | 0 | 0 | 0 | 0 | 0 | 0 | 0 | ... |
| | | ... | ... | ... | ... | ... | ... | ... | ... |
| ... | | | | | | | | | |

| fc1 CHANGE | fc1 Q FACTOR CHANGE | fc2 CHANGE | fc2 Q FACTOR CHANGE | fc3 CHANGE | fc3 Q FACTOR CHANGE | ... |
|---|---|---|---|---|---|---|
| +0.11[Hz] | 0 | 0 | 0 | 0 | 0 | ... |

| PORTION | CHANGE PARAMETER | CHANGE INFORMATION | | | | | |
|---|---|---|---|---|---|---|---|
| | | fc1 CHANGE | fc1 Q FACTOR CHANGE | fc2 CHANGE | fc2 Q FACTOR CHANGE | fc3 CHANGE | fc3 Q FACTOR CHANGE |
| FIRST BRANCH | DIAMETER +10.0[mm] | 0 | 0 | +0.3[Hz] | 0 | 0 | 0 |
| | ⋮ | ⋮ | ⋮ | ⋮ | ⋮ | ⋮ | ⋮ |
| | HEIGHT +10.0[mm] | 0 | 0 | −0.2[Hz] | 0 | 0 | 0 |
| | ⋮ | ⋮ | ⋮ | ⋮ | ⋮ | ⋮ | ⋮ |
| | NUMBER OF LEAVES +1[枚] | 0 | Qsub1 | 0 | 0 | 0 | 0 |
| | ⋮ | ⋮ | ⋮ | ⋮ | ⋮ | ⋮ | ⋮ |
| | FRUIT WEIGHT +0.5[kg] | 0 | Qsub2 | 0 | 0 | 0 | 0 |
| | ⋮ | ⋮ | ⋮ | ⋮ | ⋮ | ⋮ | ⋮ |
| ⋯ | ⋯ | ⋯ | ⋯ | ⋯ | ⋯ | ⋯ | ⋯ |

Fig. 13

| PORTION | CHANGE PARAMETER | | CHANGE INFORMATION | | | | | |
|---|---|---|---|---|---|---|---|---|
| | | | fc1 CHANGE | fc1 Q FACTOR CHANGE | fc2 CHANGE | fc2 Q FACTOR CHANGE | fc3 CHANGE | fc3 Q FACTOR CHANGE | ... |
| FIRST LEAF | AREA | ... | ... | ... | ... | ... | ... | ... |
| | | +10.0[mm²] | 0 | Qsub3 | 0 | 0 | 0 | 0 |
| | | ... | ... | ... | ... | ... | ... | ... |
| | ... | ... | ... | ... | ... | ... | ... | ... |

131

Fig. 16
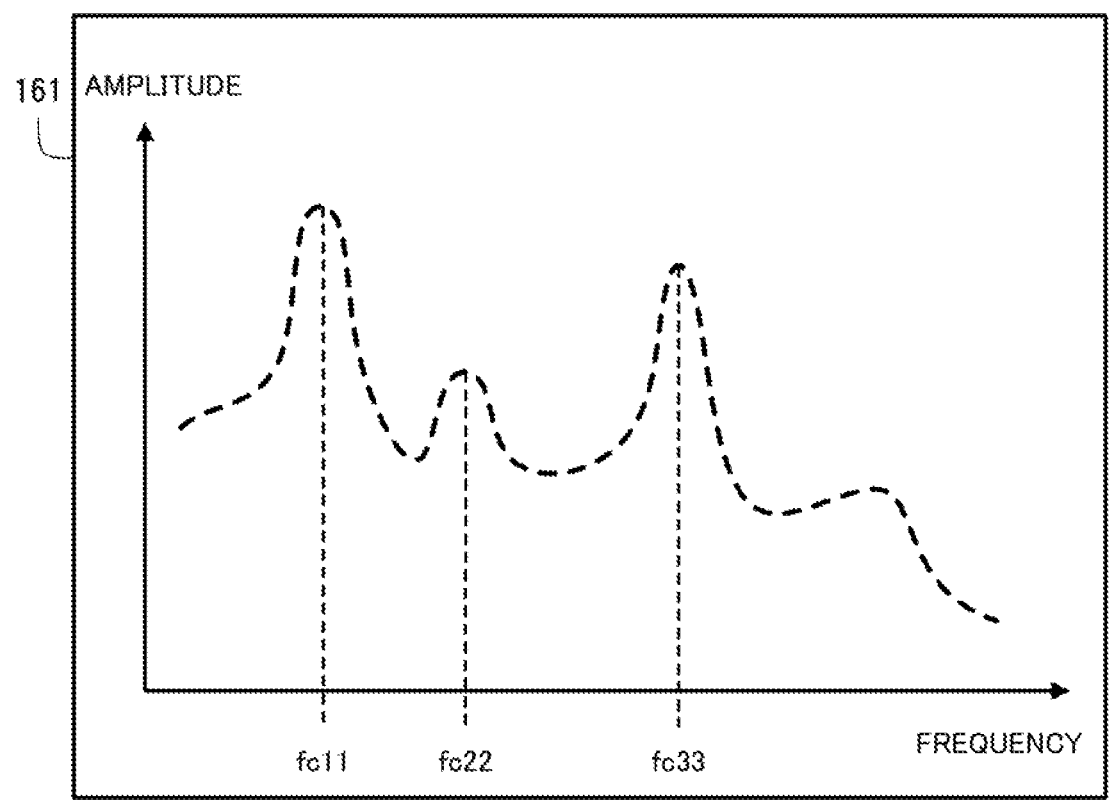
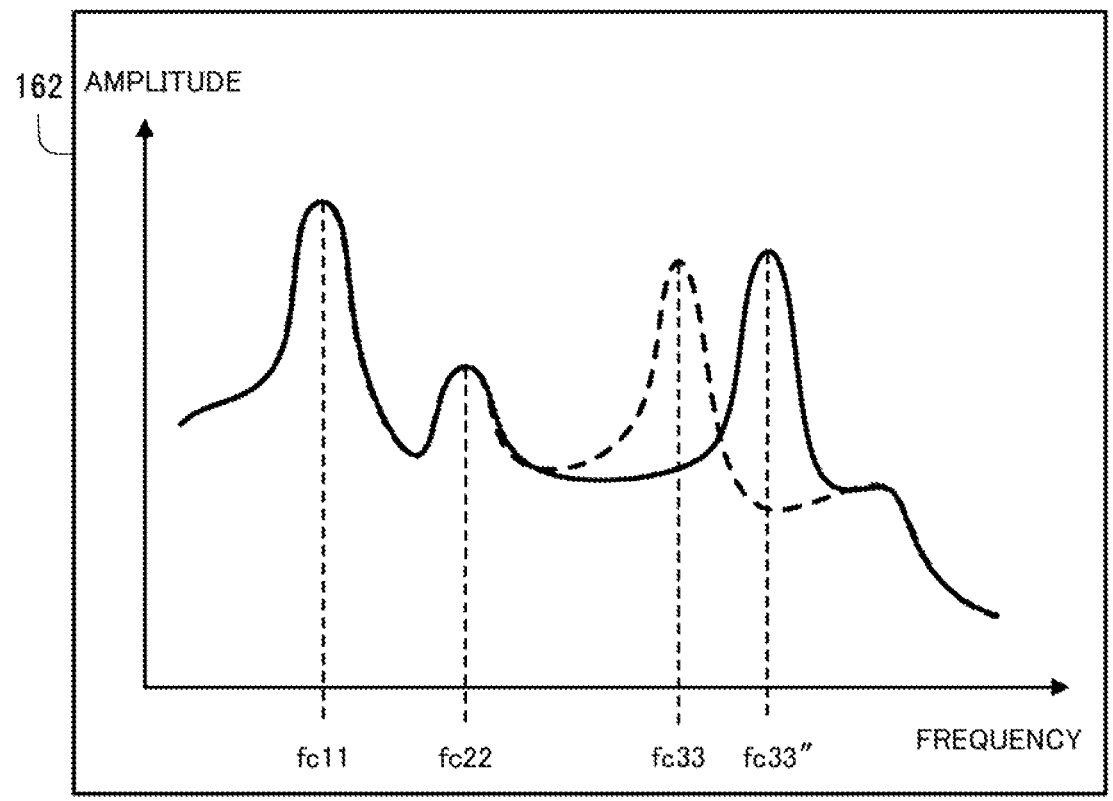

Fig. 17

| PORTION | CHANGE PARAMETER | CHANGE INFORMATION | | | | | | |
|---|---|---|---|---|---|---|---|---|
| | | fc1 CHANGE | fc1 Q FACTOR CHANGE | fc2 CHANGE | fc2 Q FACTOR CHANGE | fc3 CHANGE | fc3 Q FACTOR CHANGE | ... |
| ... | ... | ... | ... | ... | ... | ... | ... | ... |
| FRUIT | +0.5[kg] WEIGHT | 0 | 0 | 0 | 0 | +0.3[Hz] | 0 | ... |
| ... | ... | ... | ... | ... | ... | ... | ... | ... |
| | | ... | ... | ... | ... | ... | ... | ... |

| fc1 CHANGE | fc1 Q FACTOR CHANGE | fc2 CHANGE | fc2 Q FACTOR CHANGE | fc3 CHANGE | fc3 Q FACTOR CHANGE | ... |
|---|---|---|---|---|---|---|
| 0 | 0 | 0 | 0 | +0.33[Hz] | 0 | ... |

181

PLANT MONITORING APPARATUS, PLANT MONITORING METHOD, AND COMPUTER-READABLE RECORDING MEDIUM

INCORPORATION BY REFERENCE

This application is based upon and claims the benefit of priority from Japanese patent application No. 2019-046895, filed on Mar. 14, 2019, the disclosure of which is incorporated herein in its entirety by reference.

BACKGROUND OF THE INVENTION

1. Technical Field

The present invention relates to a plant monitoring apparatus and a plant monitoring method for monitoring plants, and also relates to a non-transitory computer-readable recording medium that stores a program for realizing the plant monitoring apparatus and the plant monitoring method.

2. Background Art

In order to monitor the growth of a plant, a method is known in which plant growth is monitored using an image capturing apparatus. For example, JP 2015-202056A discloses a system for monitoring the growth of a plant with use of captured images of the plant. According to this system for monitoring plant growth, images that correspond to a reference marker provided on a plant and a predetermined portion (measurement target) of the plant are extracted from a captured image of the plant, and the distance from the reference marker to the target portion is measured in order to monitor the growth of the plant.

Also, as related technology, JP 2015-112083A discloses an apparatus for ascertaining the health of a plant. According to this apparatus, vibration is applied to a plant with use of a vibration source, and changes in the plant are specified based on vibration measured via the plant in order to ascertain the health of the plant.

However, the plant growth monitoring system disclosed in JP 2015-202056A uses an image capturing apparatus, and therefore cannot monitor plant growth if it is not possible to capture images of the reference marker provided on the plant or the predetermined portion (measurement target) of the plant. One conceivable example is the case where a leaf, a stalk, or the like of the target plant or another plant grows and blocks the reference marker or the measurement target of the target plant in the captured image of the target plant.

Also, the plant health ascertaining apparatus disclosed in JP 2015-112083A forcibly applies vibration to the plant with use of the vibration source, and this can influence the growth of the plant. Moreover, if vibration is not forcibly applied to the plant, the health of the plant cannot be ascertained at all times.

Also, although JP 2015-202056A and JP 2015-112083A disclose the monitoring of the growth and the health state of a plant above the soil surface, they do not disclose the monitoring of the soil state.

SUMMARY

An example object of the present invention is to provide a plant monitoring apparatus, a plant monitoring method, and a program for monitoring the state of a plant and the soil in which the plant grows.

In order to achieve the aforementioned object, a plant monitoring apparatus according to an example aspect of the present invention includes:

a soil state estimating unit that estimating a state of soil by, with use of frequency association information calculated based on vibration measured via the soil, referencing soil state estimation information in which the frequency association information and information indicating states of the soil are associated with soil states; and a plant state estimating unit that estimating a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface.

Also, in order to achieve the aforementioned object, a plant monitoring method according to an example aspect of the present invention includes:

(a) estimating a state of soil by, with use of frequency association information calculated based on vibration measured via the soil, referencing soil state estimation information in which the frequency association information and information indicating states of the soil are associated with soil states; and (b) estimating a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface.

Furthermore, in order to achieve the aforementioned object, a non-transitory computer readable recording medium according to an example aspect of the present invention includes:

(a) a step of estimating a state of soil by, with use of frequency association information calculated based on vibration measured via the soil, referencing soil state estimation information in which the frequency association information and information indicating states of the soil are associated with soil states; and (b) a step of estimating a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface.

As described above, the present invention enables monitoring the state of a plant and the soil in which the plant grows.

BRIEF DESCRIPTION OF THE DRAWINGS

FIG. 4 is a diagram showing an example of the data structure of selected time generation information.

FIG. 6 is a diagram showing an example of the data structure of soil estimation information.

FIG. 8 is a diagram showing an example of the data structure of a growth model.

FIG. 9 is a diagram showing an example of the data structure of change information.

FIG. 11 is a diagram showing an example of the data structure of a growth model in Example Variation 1.

FIG. 13 is a diagram showing an example of the data structure of a growth model in Example Variation 2.

FIG. 16 is a diagram for describing the frequency responses and the resonance frequencies of transfer functions of plant models.

FIG. 17 is a diagram showing an example of the data structure of a growth model.

FIG. 18 is a diagram showing an example of the data structure of change information.

EXEMPLARY EMBODIMENTS

Example Embodiment

An example embodiment of the present invention will be described below with reference to FIGS. 1 to 24.

[Apparatus Configuration]

Figure 1:
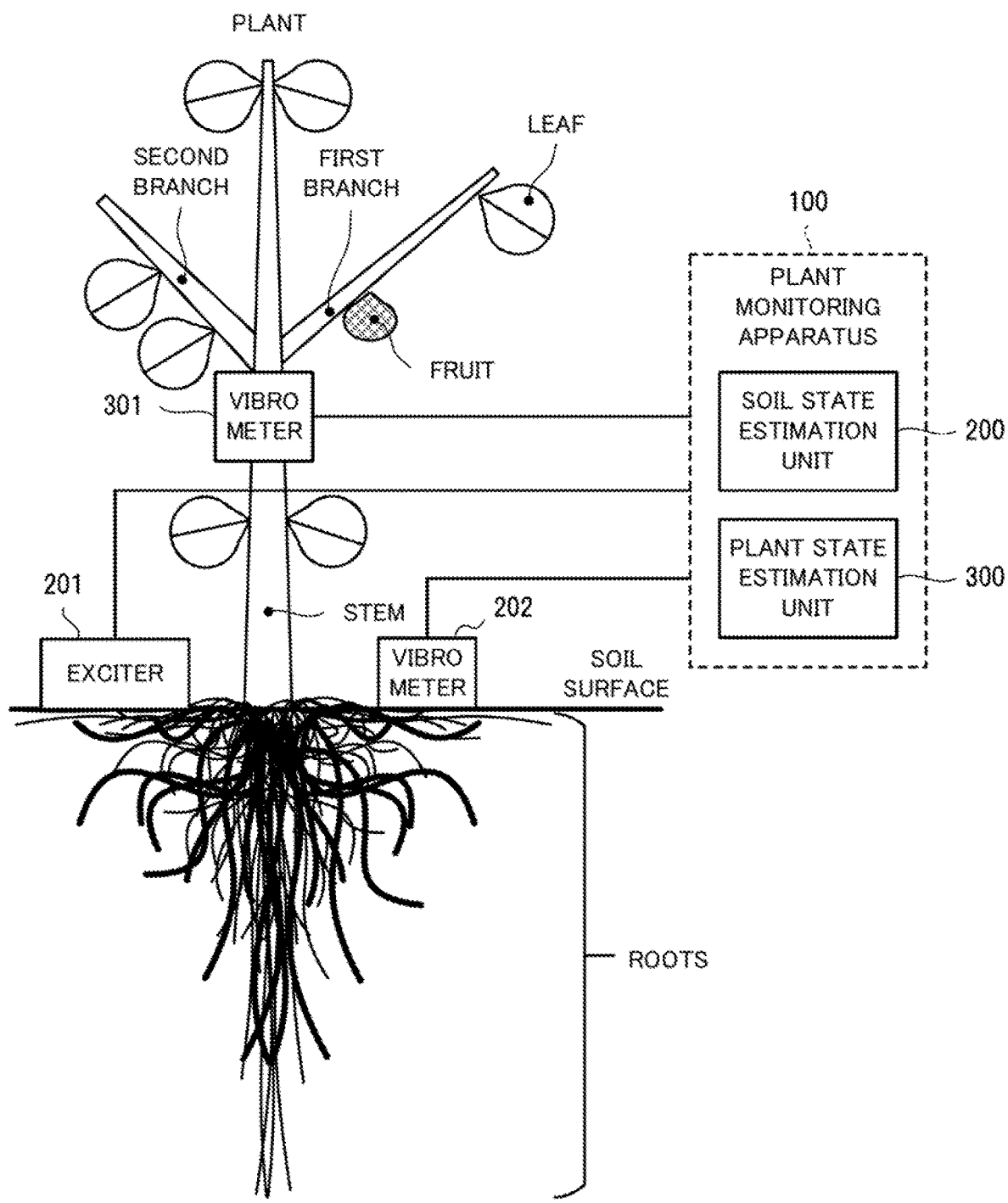
FIG. 1 is a diagram showing an example of a plant monitoring apparatus.

First, the configuration of a plant monitoring apparatus 100 of the present example embodiment will be described using FIG. 1. FIG. 1 is a diagram showing an example of the plant monitoring apparatus.

The plant monitoring apparatus 100 shown in FIG. 1 is an apparatus that monitors the state of a plant and the soil in which the plant grows. Also, as shown in FIG. 1, the plant monitoring apparatus 100 includes a soil state estimation unit 200 and a plant state estimation unit 300.

The soil state estimation unit 200 estimates a soil state by, with use of frequency association information calculated based on vibration measured via soil, referencing soil state estimation information in which the frequency association information and information indicating states of the soil are associated with soil states.

The frequency association information is a resonance frequency in a frequency response calculated from vibration, or indicates how damped the resonance frequency is (Q factor), for example. Also, the soil state estimation information is information in which the soil root quantity, soil hardness, soil moisture content, soil composition, or any combination thereof is associated with frequency association information. Note that the vibration measured via soil is produced in the soil with use of an exciter 201 and measured with use of a vibrometer 202.

The plant state estimation unit 300 estimates a plant state by, with use of growth association information that is calculated based on plant vibration and indicates plant growth, referencing plant state estimation information (a later-described growth model) in which the growth association information and information indicating states of a plant above the plant soil surface are associated with plant states above the plant soil surface.

The growth association information is information indicating plant growth, and as one example, indicates the difference (change) between a feature amount in a frequency response of vibration of the target plant and a reference feature amount that corresponds to a reference plant state. The plant state estimation information is information in which a stem state, a branch state, a leaf state, a fruit state, or any combination thereof is associated with growth association information. Note that plant vibration is measured with use of a vibrometer 301. It should be noted that any number of vibrometers may be provided.

In this way, in the present example embodiment, the use of the plant monitoring apparatus makes it possible for a user to understand the state of soil in which a plant grows and the state of the plant above the soil surface based on vibration measured via the soil and vibration produced above the target plant soil surface. In other words, the user can understand the state of the plant above the soil surface and below the soil surface.

[System Configuration]

Figure 2:
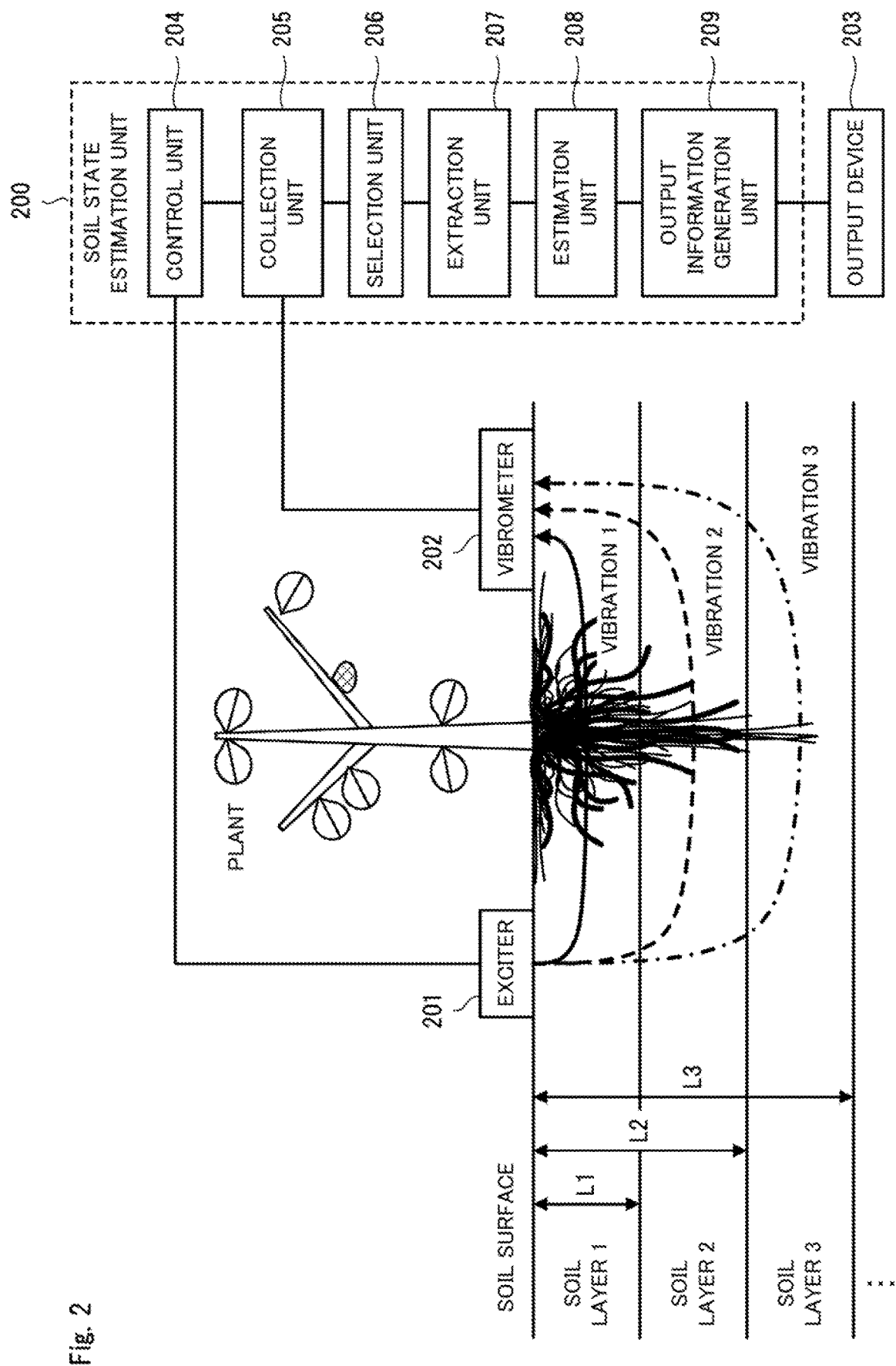
FIG. 2 is a diagram showing an example of a system that includes the plant monitoring apparatus.
Figure 3:
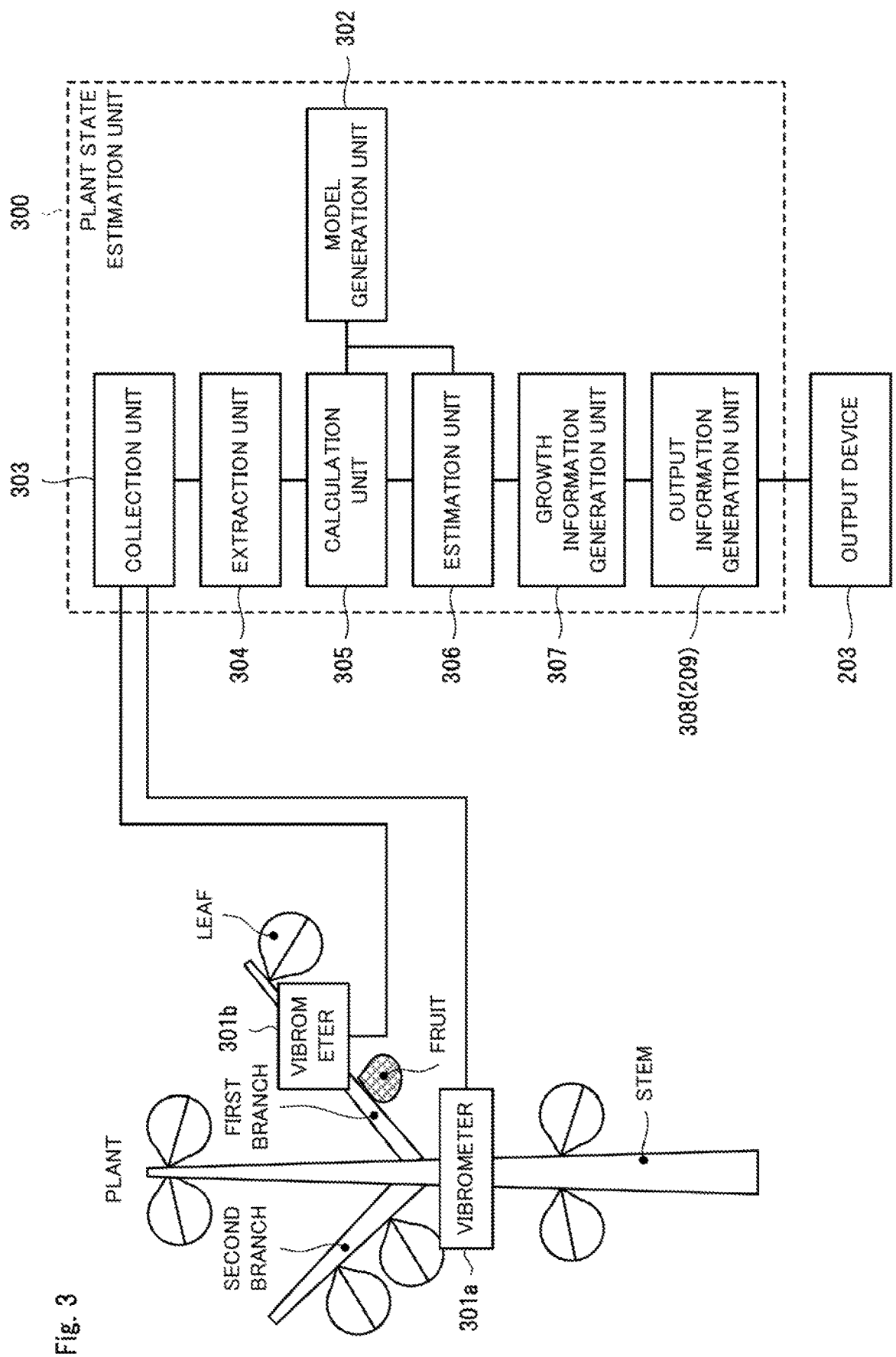
FIG. 3 is a diagram showing an example of a plant state estimation unit.

Next, the configuration of the plant monitoring apparatus 100 of the present example embodiment will be described in more detail with reference to FIGS. 2 and 3. FIG. 2 is a diagram showing an example of the soil state estimation unit. FIG. 3 is a diagram showing an example of the plant state estimation unit.

The soil state estimation unit 200 shown in FIG. 2 is an apparatus for estimating a state in accordance with a soil depth. Also, as shown in FIG. 2, the soil state estimation unit 200 of the present example embodiment includes a control unit 204, a collection unit 205, a selection unit 206, an extraction unit 207, an estimation unit 208, and an output information generation unit 209.

First, the soil state estimation unit 200 applies vibration to the soil with use of the exciter 201, measures the vibration via the soil with use of the vibrometer 202, and calculates frequency association information based on the measured vibration. Next, the soil state estimation unit 200 estimates a soil state by, with use of the calculated frequency association information, referencing soil state estimation information in which frequency association information is associated with soil states. Next, the soil state estimation unit 200 outputs the estimated soil state to the output device 203 for presentation to the user.

The plant state estimation unit 300 shown in FIG. 3 is an apparatus that monitors the state of a plant with use of vibration of the plant. Also, as shown in FIG. 3, the plant state estimation unit 300 of the present example embodiment includes a model generation unit 302, a collection unit 303, an extraction unit 304, a calculation unit 305, an estimation unit 306, a growth information generation unit 307, and an output information generation unit 308 (209).

First, the plant state estimation unit 300 calculates growth association information that indicates plant growth based on vibration of the plant measured using a vibrometer 301a or 301b or both of them. Next, the plant state estimation unit 300 estimates a plant state by, with use of the calculated growth association information, referencing plant state estimation information in which growth association information is associated with plant states above the plant soil surface. Next, the plant state estimation unit 300 outputs the estimated plant state to the output device 203 for presentation to the user.

[System Configuration Regarding Soil State Estimation Unit]

Devices used by the soil state estimation unit 200 will be described in detail below with reference to FIG. 2.

The exciter 201 is an apparatus used to apply vibration to soil. Specifically, the exciter 201 is arranged on the soil surface, and produces vibration in the soil. First, the exciter 201 acquires, from the control unit 204, vibration setting information that is used to set the vibration of the exciter 201. The vibration setting information is information for setting the vibration strength, the vibration frequency, and the like.

Next, upon acquiring the vibration setting information from the control unit 204, the exciter 201 produces vibration in the soil based on the vibration setting information. One example of the vibration method is a method in which the vibration frequency is swept such that vibration having various frequencies is produced in the soil.

Note that the exciter 201 may conceivably be a mechanical, hydraulic, electric, piezoelectric, electromagnetic exciter or the like, or may be a hammer, for example. Also, it is sufficient that the exciter 201 can produce vibration to the extent of not causing the collapse of ridges or the like formed in soft soil in a field or the like. Also, the exciter 201 communicates with the control unit 204 via wireless communication, wired communication, or the like.

The vibrometer 202 is an apparatus that measures vibration applied to the soil. Specifically, the vibrometer 202 is arranged on the soil surface, and measures, via the soil, vibration that has been applied to the soil by the exciter 201. The vibrometer 202 then outputs vibration information, which indicates the measured vibration, to the collection unit 205.

Note that the vibrometer 202 may conceivably be a mechanical, electromagnetic, piezoelectric, optical, or electromagnetic wave vibrometer, for example. The vibrometer 202 and the collection unit 205 communicate with each other through wireless communication or wired communication, for example.

The output device 203 acquires output information, which is information that has been converted into an outputtable format by the output information generation unit 209, and outputs an image, audio, or the like that has been generated based on the output information. For example, the output device 203 is a liquid crystal, organic EL (Electro Luminescence), CRT (Cathode Ray Tube), or other type of image display device. Furthermore, the image display device may include an audio output device such as a speaker. Note that the output device 203 may also be a printing device such as a printer. The output information will be described later.

The soil state estimation unit 200 will be described in detail below.

The control unit 204 controls at least the exciter 201 and the collection unit 205. Specifically, the control unit 204 controls the vibration produced by the exciter 201 by transmitting the vibration setting information to the exciter 201. The control unit 204 also causes the collection unit 205 to start collecting vibration information by transmitting a vibration start instruction to the collection unit 205.

The collection unit 205 collects vibration information from the vibrometer 202. Specifically, first, the collection unit 205 collects vibration information from the vibrometer 202 in a time series. The collection unit 205 then outputs the collected vibration information to the selection unit 206. The collection unit 205 also stores the vibration information in a storage unit (not shown). The storage unit may be provided in the soil state estimation unit 200, or may be provided outside the soil state estimation unit 200.

Using the transmission time for which vibration passed through the soil, the selection unit 206 selects vibration that was measured via the soil at a certain soil depth. Specifically, vibration that corresponds to a certain soil depth is selected with use of the fact that the transmission time is different according to soil depth.

Here, soil depth is indicated by the distance from the surface of the soil (soil surface) in the vertical direction. In the example in FIG. 2, a soil layer 1 is the layer of soil extending to a distance L1 from the soil surface, a soil layer 2 is the layer of soil extending from the distance L1 to a distance L2, and a soil layer 3 is the layer of soil extending from a distance L3 to the distance L2.

The transmission time is specifically the amount of time from the time when vibration was applied to a target soil surface until the time when vibration corresponding to that vibration is measured at the soil surface. As shown in FIG. 2, the vibration applied to the soil is conceivably vibration that is applied by the exciter 201 arranged on the soil surface, for example. As shown in FIG. 2, the vibration that passes through the soil and is transmitted to the soil surface is measured by the vibrometer 202 arranged on the soil surface, for example.

Also, the deeper the soil is, the longer the transmission time is, and therefore as shown in FIG. 2, a transmission time T1 of vibration 1 (solid line) transmitted to the vibrometer 202 via the soil layer 1, a transmission time T2 of vibration 2 (dashed line) transmitted to the vibrometer 202 via the soil layer 2, and a transmission time T3 of vibration 3 (dashed-dotted line) transmitted to the vibrometer 202 via the soil layer 3 satisfy the relationship T3>T2>T1.

Specifically, first, the selection unit 206 acquires vibration information from the collection unit 205. Next, the selection unit 206 calculates a selected time based on the transmission time that corresponds to the target soil layer. For example, in the case of selecting vibration information that corresponds to the soil layer 1, using the transmission time T1 that corresponds to the soil layer 1, the selected time is calculated as the duration from when vibration is produced by the exciter 201 in the soil until when vibration 1 reflected by the soil layer 1 is measured by the vibrometer 202.

Specifically, letting the transmission time T1 be expressed by a time te1 at which vibration produced in the soil surface at a time t0 is measured at the soil surface after passing through the soil layer 1, a selected time ts1 corresponding to the soil layer 1 is the duration from a time before the time te1 (te1−a1) until when vibration reflected by the soil layer 1 is no longer measured (te1+b1).

Note that the time a1 (start information) and the time b1 (end information) are obtained by experimentation, simulation, or the like. Also, selected times ts2, ts3, and so on for the other soil layers 2, 3, and so on are calculated similarly to the case of the soil layer 1.

FIG. 4 is a diagram showing an example of the data structure of selected time generation information. The above-described transmission time, start information, and end information for each soil layer are stored in advance in a storage unit in association with the corresponding soil layers, as shown in selected time generation information 41 shown in FIG. 4, for example.

Alternatively, soil layers and selected times may be stored in association with each other in the storage unit in advance, as shown in selected time generation information 42 in FIG. 4.

Next, using the selected time, the selection unit 206 selects vibration information that corresponds to the target soil layer from the acquired vibration information. Specifically, the selection unit 206 selects the vibration information that was measured in the selected time that corresponds to the target soil layer.

The extraction unit 207 extracts a vibration feature from the selected vibration information. One conceivable example of a vibration feature is a resonance frequency.

Specifically, first, the extraction unit 207 acquires reference vibration information (input value x(t)), which is reference information that corresponds to vibration produced in the soil by the exciter 201, and vibration information (output value y(t)) that corresponds to the soil layer selected by the selection unit 206. The reference vibration information is obtained by experimentation, simulation, or the like, and is stored in the storage unit.

Also, the reference vibration information may be generated based on soil vibration that is measured by a vibrometer different from the vibrometer 202 immediately after being produced.

Next, the extraction unit 207 calculates a function that expresses the relationship between the input value x(t) and the output value y(t) that corresponds to the input value x(t). For example, a transfer function G(s) is calculated. The input value x(t) and the output value y(t) are subjected to Laplacian conversion, and the transfer function G(s) is expressed by the ratio (Y(s)/X(s)) between the resulting input value X(s) and output value Y(s). Here, the ratio expresses how the vibration was transmitted through the soil.

Figure 5:
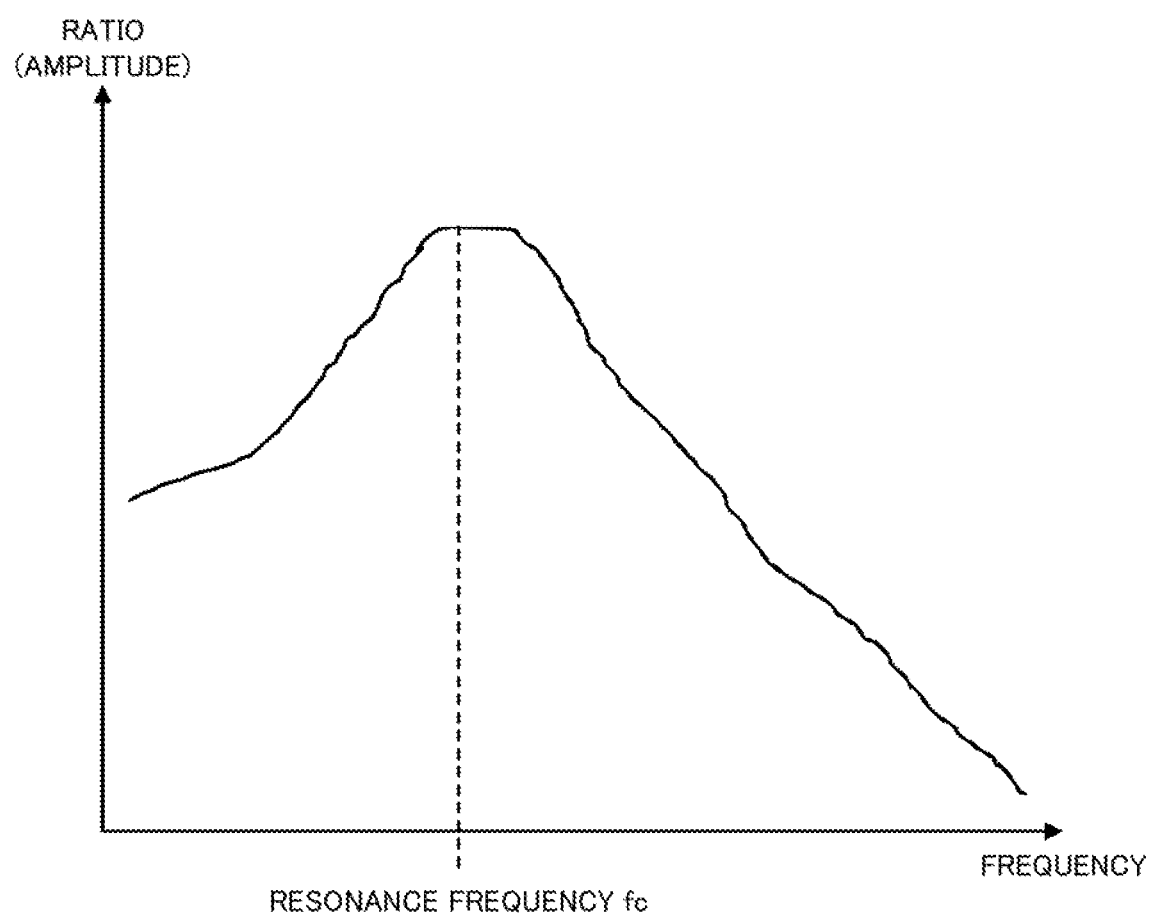
FIG. 5 is a diagram for describing a resonance frequency.

Next, using the relationship between the frequency (sweeped frequency) and the ratio (amplitude) that correspond to the vibration, the extraction unit 207 extracts the frequency that corresponds to the peak of the ratio as the vibration feature. For example, as shown in FIG. 5, the frequency that corresponds to the peak of the ratio is the resonance frequency. FIG. 5 is a diagram for describing a resonance frequency.

Note that the reason for using the resonance frequency is that because the resonance frequency changes according to the soil state, the soil state can be estimated with use of the relationship between soil states and resonance frequencies.

Note that the vibration feature is not limited to being obtained by the above-described method, and may be a vibration feature other than the resonance frequency. For example, besides the resonance frequency, the vibration feature may also be information indicating how damped the resonance frequency is (Q factor). The reason for using information that indicates the sharpness of the resonance frequency is that because the sharpness of the resonance frequency changes according to the soil state, the soil state can be estimated with use of the relationship between soil states and resonance frequency sharpness.

The estimation unit 208 references the soil estimation information using the extracted feature, and estimates the soil state. Specifically, first, the estimation unit 208 acquires the feature from the extraction unit 207. Next, using the acquired feature, the estimation unit 208 references the soil estimation information in which features and soil states are associated with each other, and estimates the soil state. The soil estimation information is stored in the storage unit (not shown) in advance, for example.

FIG. 6 is a diagram showing an example of the data structure of the soil estimation information. Soil estimation information 61 shown in FIG. 6 is information in which soil hardness [kg/m$^2$], soil root quantity [m/m$^3$], soil moisture content [%], soil composition, or any combination thereof is associated with the resonance frequency [Hz] as the feature. Note that the soil states are not limited to the information described above.

The higher the soil hardness is, the higher the resonance frequency is. The reason for this is that hard soil exerts high restoration force against external force, and therefore the resonance frequency is higher for hard soil. Also, the higher the soil root quantity is, the higher the resonance frequency is. The reason for this is that, although the way in which the resonance frequency changes as the root quantity increases is dependent on the type of root and the type of soil, it is thought that if the roots have a higher tension than the soil, then the greater the root quantity is, the higher the resonance frequency is. Also, it is thought that the higher the soil moisture content is, the lower the resonance frequency is. The reason for this is that it is generally thought that a fluid such as water has lower tension than soil. Also, the soil composition (e.g., clay, silt, sand) changes according to the resonance frequency.

Also, various contributing factors may exist for the same resonance frequency. For example, in the case of the resonance frequency of 10 [Hz], there may be the case "hardness 1000 [kg/m$^2$], root quantity 1.0 [m/m$^3$], moisture content 10 [%], clay", or there may be the case "hardness 2000 [kg/m$^2$], root quantity 1.0 [m/m$^3$], moisture content 30 [%], clay". In such a case, the hardness may be determined using a method for something other than hardness, such as using crop simulation, a moisture content sensor, soil analysis, or the like to specify the root quantity, moisture content, and soil composition, and then determine the hardness based on the specified results.

Alternatively, it is conceivable to increase the number of dimensions in terms of the vibration feature. In the case of increasing the number of dimensions in terms of the vibration feature, it is conceivable to further specify a resonance frequency Q factor as a feature amount, or measure multiple resonance frequencies. According to such a configuration, it is possible to distinguish between different soil states even when there are multiple sets of contributing factors for the same resonance frequency.

The output information generation unit 209 outputs the soil state that corresponds to the soil layer to the output device 203. Specifically, first, the output information generation unit 209 acquires information indicating the soil state from the estimation unit 208. Next, the output information generation unit 209 generates output information for causing the output device 203 to output the selected soil layer and the soil state that corresponds to that soil layer. The output information generation unit 209 then outputs the generated output information to the output device 203, and causes the output device 203 to output the soil state that corresponds to the soil layer.

[Effects of Soil State Estimation Unit]

As described above, vibration that corresponds to a certain soil depth can be selected using the soil state estimation unit 200, and therefore it is possible to estimate the soil state at a target depth (soil layer) with use of vibration that corresponds to that soil layer.

Also, according to the soil state estimation unit 200, measurement such as that shown in the gain line chart of FIG. 5 is sufficient, and therefore integration can be performed with a weak continuous wave. By using the exciter 201 to intermittently or continuously apply weak vibration to the soil, it is possible to raise the SN ratio of the statistically measured vibration. For this reason, it is possible to estimate the soil state of soft soil in a field or the like without causing ridges or the like to collapse.

Furthermore, speed is not measured, and therefore a strong shock is not necessary, thus making it possible to perform measurement with the vibrometer 202 that is arranged very close to the exciter 201. In other words, with a conventional method in which hardness is measured using the transmission speed of vibration, it is necessary to detect the speed difference, that is to say the vibration transmission time difference. Also, the vibration source and the measurement location need to be separated far enough to be able to measure a time difference, and therefore strong vibration needs to be applied.

However, with the soil state estimation unit 200, there is no need to detect a speed difference, and it is sufficient to intermittently or continuously produce vibration with use of the exciter 201, measure the vibration with the vibrometer 202, and then determine the magnitude of the measured vibration, and therefore measurement can be performed with the vibrometer 202 that is arranged very close to the exciter 201.

Also, because the soil state can be estimated, outputting the soil state to the output device 203 makes it possible for a worker to take an appropriate action on the target soil layer. As one example of an appropriate action, if the soil is hard, the worker can be prompted to plow the soil, for example.

[System Configuration Regarding Plant State Estimation Unit]

Devices used by the plant state estimation unit 300 will be described in detail below with reference to FIG. 3.

The vibrometers 301 (301a, 301b, or both) are apparatuses that measure vibration of a plant that occurs due to external force. Specifically, the vibrometer 301 first measures plant vibration. The vibrometer 301 then outputs vibration information, which indicates the measured vibration, to the collection unit 303. External force refers to a force that applies vibration to the plant from the outside, such as wind, soil shifting, or the like. Note that the external force may apply vibration to the plant with use of an exciter or the like. It should be noted that in the case of using an exciter or the like, it is desirable that the applied vibration does not influence plant growth.

Also, the vibrometer 301 may conceivably be a mechanical, electromagnetic, piezoelectric, optical, or electromagnetic wave vibrometer, for example. The vibrometer 301 may also be a high-sensitivity vibration sensor such as a microphone or a miniature Michelson interferometer, for example. The vibrometer 301 and the plant monitoring apparatus 100 communicate with each other through wireless communication or wired communication, for example.

The plant state estimation unit 300 will be described in detail below.

The model generation unit 302 executes a growth model simulation on a target plant in order to generate a growth model of the target plant, and stores the growth model in a storage unit (not shown). The storage unit that stores the growth model may be provided in the plant monitoring apparatus 100, or may be provided outside the plant monitoring apparatus 100.

The growth model simulation is for calculating a feature amount of the target plant in a reference state (reference feature amount) and a feature amount that changes along with growth (growth feature amount), associating change in the growth feature amount relative to the calculated reference feature amount with a plant state, and storing the result as a growth model.

Here, assuming that estimation of the growth state of the target plant is performed at a time t0, the reference state is a state of the target plant at a time that is at least before the time t0.

The following describes feature amount calculation in the growth model simulation.

(a1) First, the model generation unit 302 models the target plant in order to generate plant models. The model generation unit 302 generates a plant model for the reference state and various possible states of growth of the target plant after the reference state. Conceivable examples of various possible states of growth include a state where the stem has grown upward and a state where the stem has increased in diameter.

Also, the plant model is obtained with use of a numerical model that uses a finite element method or a mathematical model that uses a mathematical expression, for example. In the case of using a finite element method, the plant is considered to be a collection of small elastic bodies, and dynamic computation is performed for each element. If using a mathematical model, in the case of the stem of a plant growing from the ground for example, maximum approximation is performed considering the stem to be an inverted pendulum with a fixed lower portion that has restoring force, and the approximated equation of motion is used in the mathematical model.

(a2) Next, the model generation unit 302 applies vibration to some or all of the generated plant models (including the reference state) by virtually applying pre-set vibration for a pre-set time. The model generation unit 302 then measures the vibration and generates vibration information. Note that it is desirable that vibration in the plant model is measured at a position that corresponds to the position on the target plant where vibration is actually measured by the vibrometer 301. It should be noted that the position where vibration is measured in the plant model is not required to be the same as the position on the target plant where the vibrometer 301 performs measurement.

Figure 7:
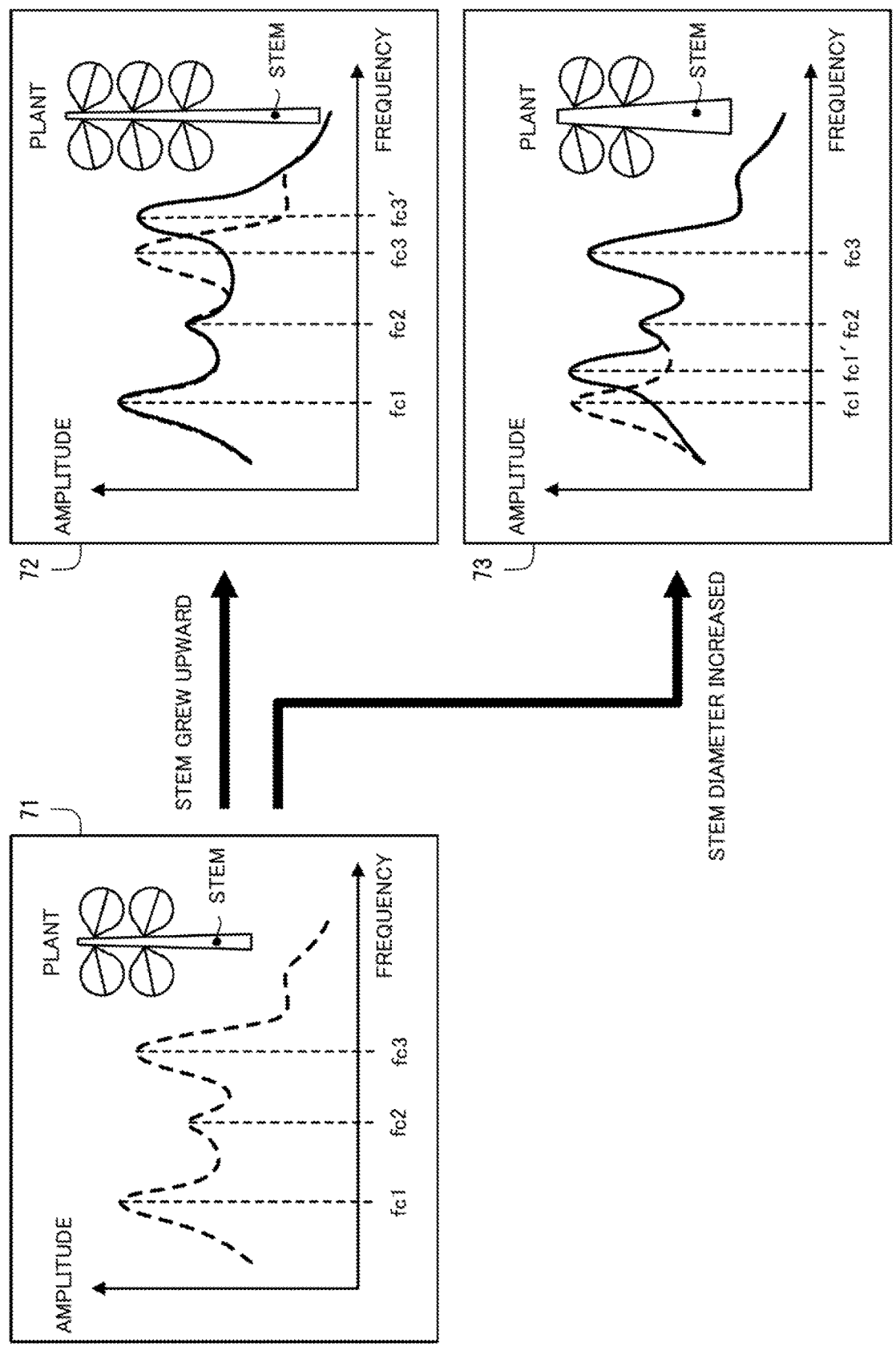
FIG. 7 is a diagram for describing the frequency responses and the resonance frequencies of plant models.

(a3) Next, the model generation unit 302 converts the vibration information of the generated plant models from the time domain to the frequency domain (e.g., Fourier transform) in order to generate frequency response information that indicates frequency responses as shown in FIG. 7.

FIG. 7 is a diagram for describing the frequency responses and the resonance frequencies of plant models. A graph 71 in FIG. 7 shows the frequency response of a plant model in the reference state. A graph 72 shows the frequency response of a plant model in the case where the stem of the target plant has grown upward. A graph 73 shows the frequency response of a plant model in the case where the stem of the target plant has increased in diameter.

(a4) Next, using the frequency responses of the generated plant models, the model generation unit 302 extracts, as the feature amount, either the resonance frequency or a value indicating how damped the resonance frequency is (Q factor), or both of them, from the frequency response. It should be noted that the feature amount is not limited to being the resonance frequency or the Q factor.

The graph 71 in FIG. 7 shows resonance frequencies fc1, fc2, and fc3. The graph 72 shows that the resonance frequency fc3 changes to fc3' in accordance with plant growth. The graph 33 shows that the resonance frequency fc1 changes to fc1' in accordance with plant growth.

(a5) Next, the model generation unit 302 generates plant model feature information for each plant model by associating identification information that identifies the plant model, the states of portions of the plant model, and one or more feature amounts with each other. Note that the states of portions refers to information indicating states such as the stem diameter, the stem height, and the stem inclination.

(a6) Next, the model generation unit 302 calculates the difference (change) between a feature amount that corresponds to the plant model feature information for the reference state (reference feature amount) and a feature amount that corresponds to the plant model feature information for a state of growth after the reference state (growth feature amount).

(a7) Next, the model generation unit 302 generates a growth model for each plant model as shown in FIG. 8 by associating the states of portions of the plant model, change parameters indicating change of portions of the plant model, and the changes of one or more feature amounts corresponding to the change parameters with each other, and stores the growth models in the storage unit.

FIG. 8 is a diagram showing an example of the data structure of a growth model. In a growth model 81 shown in FIG. 8, "portion", which indicates a portion of the plant model, "change parameter", which indicates states of the portion of the plant model, and "change information", which indicates change in the growth feature amounts corresponding to the reference feature amounts, are associated with each other.

The following describes the calculation of the change of feature amounts.

For example, as shown in FIG. 7, the resonance frequencies fc1, fc2, fc3 and so on are extracted in the reference plant model, and in the plant model where the stem of the reference plant model has grown upward, a resonance frequency occurs at the frequency fc3', which is different from the resonance frequency fc3, as shown in the graph 72 in FIG. 7. Also, in the plant model where the stem of the reference plant model has increased in diameter (the circumference of the stem has increased), a resonance frequency occurs at the frequency fc1', which is different from the resonance frequency fc1, as shown in the graph 73 in FIG. 7.

In such a case, if the diameter of the stem in the reference plant model has increased by +1.0 [mm] as in the first row of the growth model shown in FIG. 8 for example, the resonance frequency fc1' appears at a position that is shifted by +0.1 [Hz] from the resonance frequency fc1. In view of this, +1.0 [mm], which indicates the change of the diameter of the stem, which is a state of the plant ("diameter" under "change parameter"), and +0.1 [Hz], which indicates the change of the resonance frequency in the "change information" ("fc1 change"), are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "diameter", "height", "inclination" and the like), and such change information is stored as shown in the growth model 81 shown in FIG. 8.

Note that the model generation unit 302 may be provided separately from the plant monitoring apparatus 100. In this case, the system is configured such that the plant monitoring apparatus 100 and the model generation unit 302 can communicate with each other.

The following describes plant state estimation performed by the plant state estimation unit 300.

The collection unit 303 collects vibration information from the vibrometer 301 in the case where the state of the target plant is to actually be estimated. Specifically, first, the collection unit 303 collects vibration information from the vibrometer 301 in a time series, and stores the vibration information in a storage unit (not shown). The storage unit may be provided in the plant monitoring apparatus 100, or may be provided outside the plant monitoring apparatus 100.

The extraction unit 304 uses the vibration information, which indicates vibration of the target plant, to generate a frequency response regarding the vibration, and extracts feature amounts from the generated frequency response.

(b1) The extraction unit 304 acquires, from the aforementioned storage unit, vibration information corresponding to a pre-set duration at a pre-set interval. Here, the set interval and the set duration can be set as desired by the user.

(b2) Next, the extraction unit 304 converts the vibration information collected over the pre-set duration from the time domain to the frequency domain (e.g., Fourier transform) to generate frequency response information that indicates the frequency response.

(b3) Next, the extraction unit 304 extracts a feature amount from the generated frequency response. The extraction unit 304 extracts a resonance frequency or a value indicating how damped the resonance frequency is (Q factor), or both, from the frequency response. It should be noted that the feature amount is not limited to being the resonance frequency or the Q factor.

The calculation unit 305 then calculates change, which indicates plant growth, based on the feature amount that was extracted by the extraction unit 304 and a reference feature amount.

(c1) First, the calculation unit 305 acquires feature information from the extraction unit 304. The calculation unit 305 also acquires plant model feature information for the reference state from the growth model.

(c2) Next, the calculation unit 305 calculates the difference (change) between a reference feature amount in the plant model feature information for the reference state and a feature amount in the feature information that was acquired from the extraction unit 304. The calculation unit 305 generates change information 91 that indicates the change of the feature amount as shown in FIG. 9 for example, and stores the change information 91 in the storage unit. FIG. 9 is a diagram showing an example of the data structure of change information.

Alternatively, instead of using the plant model, the calculation unit 305 may use feature information of the target plant that was actually measured in the reference state as the reference feature amount, and calculate the difference (change) between that reference feature amount and a feature amount in the feature information acquired from the extraction unit 304.

Then, using the calculated change information, the estimation unit 306 estimates the state of the plant by referencing the growth model, finding change information in the growth model that is similar to the calculated change information, and selecting a plant state that corresponds to the found change information.

(d1) Using the change information 91 shown in FIG. 9 that was calculated by the calculation unit 305, the estimation unit 306 references the growth model 81 shown in FIG. 8 and extracts change information that is similar to the change information 91.

(d2) Next, the estimation unit 306 selects the "change parameter" that is associated with the extracted change information 91, and estimates the plant growth indicated by the "change parameter" as the plant state. The change information 91 is similar to the change information in the first row in the growth model 81, and therefore the estimation unit 306 selects "stem diameter+10.0 [mm]" as the plant state.

Note that in the case of the change information 91 as well, the similarity calculation is performed by a method of generating a vector that has elements of the change information 91 as vector elements. A vector that has elements of the change information as vector elements is generated for each row of the growth model 81.

The distance is then calculated between the generated vector of the change information 91 and the vectors of the rows in the growth model 81, and the vector in the growth model 81 that has the shortest distance is considered to be similar to the vector of the change information 91. The distance is a Euclidian distance, for example. It should be noted that the similarity calculation method is not limited to the method described above.

The growth information generation unit 307 generates growth information by associating the plant state estimated by the estimation unit 306 with a time that indicates the time at which the vibration information was measured. The growth information generation unit 307 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 308 (209) then uses the growth information to generate output information that is to be used for outputting the growth information to the output device 203. Thereafter, the output information generation unit 308 outputs the output information to the output device 203.

[Effects of Plant State Estimation Unit]

As described above, by using the plant state estimation unit 300, it is possible to extract a feature amount regarding a frequency response from the vibration of a portion of a target plant (e.g., a stem, a branch, or a leaf), calculate the difference (change) between a reference feature amount and the extracted feature amount, and estimate a plant state (plant growth state) based on the calculated change of the feature amount.

Also, with the plant state estimation unit 300, even when not forcibly applying vibration that influences plant growth, it is possible to use vibration of the plant caused by minute vibration from wind, soil shift, and the like, thus making it possible to monitor the state of the plant even when vibration is not being forcibly applied. This therefore makes it possible to continuously monitor the state of the plant.

Furthermore, because the state of the plant can be continuously monitored with the plant state estimation unit 300, the growth of the plant can be easily recorded. Furthermore, the state of the plant can be continuously monitored even when a worker is at a remote location.

[Example Variation 1]

Figure 10:
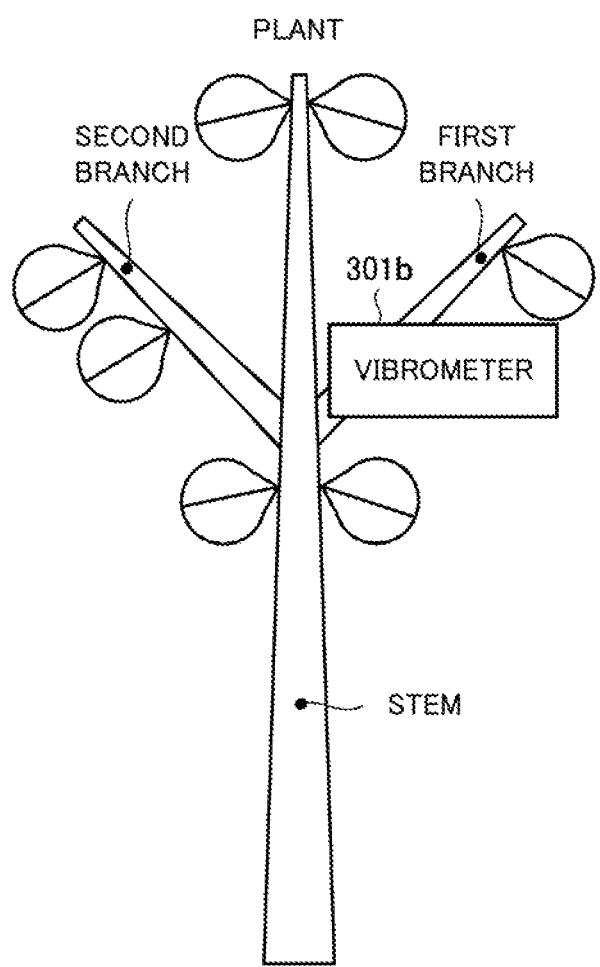
FIG. 10 is a diagram for describing the estimation of the state of a branch.

The following describes Example Variation 1. In Example Variation 1, the portion of the target plant is a branch instead of the stem. FIG. 10 is a diagram for describing the estimation of the state of a branch. Also, in the example in FIG. 10, vibration of a first branch is measured at the position of the vibrometer 301b in FIG. 10.

The following describes growth model generation in Example Variation 1.

In Example Variation 1, the model generation unit 302 executes growth model simulation on the first branch shown in FIG. 10 as the portion of the target plant, for example, in order to generate a growth model 111 that corresponds to the first branch of the target plant as shown in FIG. 11, and stores the growth model 111 in the storage unit (not shown).

FIG. 11 is a diagram showing an example of the data structure of a growth model in Example Variation 1. In the growth model 111 shown in FIG. 11, "portion", which indicates the first branch of the plant model, "change parameter", which indicates states of the first branch of the plant model, and "change information", which indicates change in growth feature amounts corresponding to the reference feature amounts, are associated with each other.

The following describes the calculation of the change of a feature amount in Example Variation 1.

In the case of the growth model 111 shown in FIG. 11, the diameter of the first branch of the reference plant model has increased by +10.0 [mm], and the resonance frequency fc2' appears at a position that is shifted by +0.3 [Hz] from the resonance frequency fc2. In view of this, +10.0 [mm], which indicates the change of the "diameter" under "change parameter", which is a state of the plant, and +0.3 [Hz], which indicates the change of the resonance frequency in "fc2 change" under "change information", are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "diameter", "height", "number of leaves", "fruit weight", and the like), and such change information is stored as shown in the growth model 111 shown in FIG. 11.

Note that Qsub1 shown in FIG. 11 is a value that indicates that the Q factor of the reference resonance frequency fc1 has changed by Qsub1 in the case where the number of leaves on the first branch has increased by +1 [leaf]. Also, Qsub2 shown in FIG. 11 is a value that indicates that the Q factor of the reference resonance frequency fc1 has changed by Qsub2 in the case where the fruit weight of the first branch has increased by +0.5 [kg].

The following describes plant state estimation in Example Variation 1.

First, the collection unit 303 collects vibration information indicating vibration of the first branch from the vibrometer 301b. Specifically, first, the collection unit 303 collects vibration information from the vibrometer 301b in a time series, and stores the vibration information in a storage unit (not shown).

Next, using the vibration information that indicates vibration of the first branch, the extraction unit 304 generates a frequency response regarding the vibration of the first branch, and extracts a feature amount of the first branch from the generated frequency response.

Next, the calculation unit 305 calculates change, which indicates growth of the first branch, based on the feature amount of the first branch that was extracted by the extraction unit 304 and a reference feature amount of the first branch. The calculation unit 305 then generates change information using the calculated change of the first branch, and stores the change information in the storage unit.

Alternatively, instead of using the plant model, the calculation unit 305 may use feature information of the first branch that was actually measured in the reference state as the reference feature amount, and calculate the difference (change) between that reference feature amount and a feature amount in the feature information acquired from the extraction unit 304.

Next, using the change information generated by the calculation unit 305, the estimation unit 306 references the growth model 111 and estimates a state of the first branch.

Next, the growth information generation unit 307 generates growth information in which the state of the first branch estimated by the estimation unit 306 and a time indicating the time at which the vibration information was measured are associated with each other. The growth information generation unit 307 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 308 then uses the growth information to generate output information that is to be used for outputting the growth information to the output device 203. Thereafter, the output information generation unit 308 outputs the output information to the output device 203.

[Effects of Example Variation 1]

As described above, according to the plant state estimation unit 300, it is possible to extract a feature amount regarding a frequency response from the vibration of a branch of a target plant, calculate the difference (change) between a reference feature amount and the extracted feature amount, and estimate a plant state (plant growth state) based on the calculated change of the feature amount.

[Example Variation 2]

The following describes Example Variation 2. In Example Variation 2, the portion of the target plant is a leaf. Specifically, in Example Variation 2, vibration generated when leaves rub against each other due to an external force is measured, and leaf growth is estimated using the measured vibration.

Figure 12:
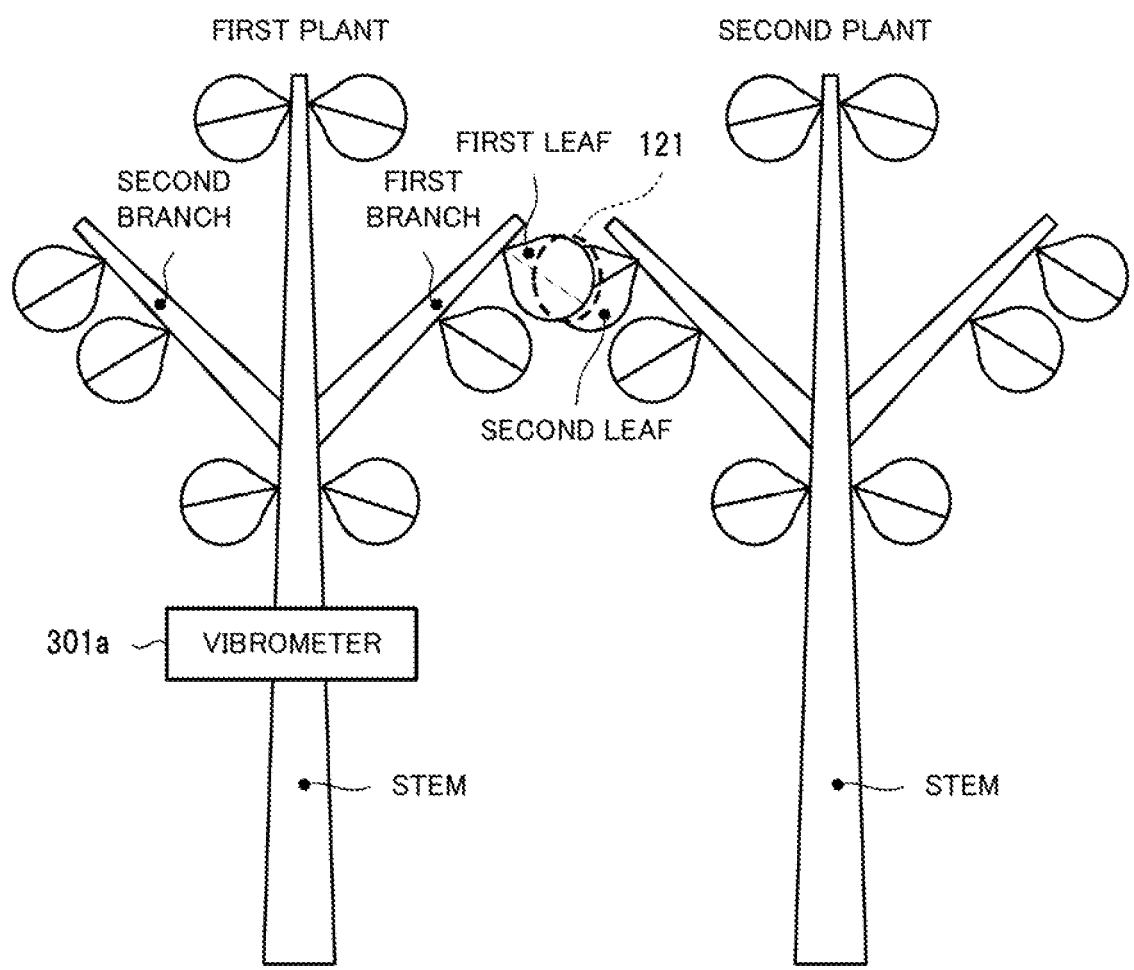
FIG. 12 is a diagram for describing the estimation of the state of a leaf.

FIG. 12 is a diagram for describing the estimation of the state of a leaf. In FIG. 12, the portion of the target plant is a leaf on the first branch as shown in FIG. 12. Also, in the example in FIG. 12, vibration generated when a first leaf and a second leaf rub against each other is measured at the position of the vibrometer 301a in FIG. 12. Note that the dashed line in FIG. 12 indicates a range 121 in which the first leaf and the second leaf rub against each other.

The following describes growth model generation in Example Variation 2.

In Example Variation 2, the model generation unit 302 executes growth model simulation on the first leaf shown in FIG. 12 as the portion of the target plant, for example, in order to generate a growth model 131 for the first leaf of the target plant as shown in FIG. 13, and stores the growth model 131 in the storage unit (not shown).

FIG. 13 is a diagram showing an example of the data structure of a growth model in Example Variation 2. In the growth model 131 shown in FIG. 13, "portion", which indicates the first leaf of the plant model, "change parameter", which indicates states of the first leaf of the plant model, and "change information", which indicates change in growth feature amounts corresponding to the reference feature amounts, are associated with each other.

In FIG. 13, "area" under "change parameter" indicates the area of the first leaf in FIG. 12, for example. Also, the vibration generated due to the first leaf rubbing against the second leaf changes according to the areas of the first leaf and the second leaf.

The following describes growth model generation in Example Variation 2.

(a1') First, the model generation unit 302 generates plant models for the first plant and the second plant in the example shown in FIG. 12. The plant models for the first plant and the second plant are generated for a reference state and various states of change in the process of growth of the first plant and the second plant. Specifically, plant models are generated for various states of overlap of the first leaf and the second leaf in the process of growth of the first leaf and the second leaf. Note that leaf overlap is not limited to the overlapping of two leaves.

(a2') Next, the model generation unit 302 virtually applies pre-set vibration for a pre-set time to the various plant models generated using the first plant and second plant, in order to apply vibration caused by the first leaf and the second leaf rubbing against each other. The model generation unit 302 then measures the vibration and generates vibration information. Note that it is desirable that vibration in the plant model is measured at a position that corresponds to the position on the target plant where vibration is actually measured by the vibrometer 301a. It should be noted that the position where vibration is measured in the plant model is not required to be the same as the position on the target plant where the vibrometer 301a performs measurement.

(a3') Next, the model generation unit 302 converts the vibration information of the various plant models generated using the first plant and the second plant from the time domain to the frequency domain (e.g., Fourier transform) in order to generate frequency response information that indicates frequency responses.

(a4') Next, using the frequency responses of the generated plant models, the model generation unit 302 extracts, as the feature amount, either the resonance frequency or a value indicating how damped the resonance frequency is (Q factor), or both of them, from the frequency response. It should be noted that the feature amount is not limited to being the resonance frequency or the Q factor.

(a5') Next, the model generation unit 302 generates plant model feature information for the area of the first leaf for each plant model by associating identification information that identifies the plant model, the states of the first leaf of the plant model (change parameters), and one or more feature amounts with each other.

(a6') Next, the model generation unit 302 calculates the difference (change) between a feature amount that corresponds to the plant model feature information for the reference state (reference feature amount) and a feature amount that corresponds to the plant model feature information for a state of growth after the reference state (growth feature amount).

(a7') Next, the model generation unit 302 generates a growth model 131 shown in FIG. 13 for each plant model by associating the states of the first leaf of the plant model, change parameters indicating change of the first leaf of the plant model, and the changes of one or more feature amounts corresponding to the change parameters with each other, and stores the growth models 131 in the storage unit.

The following describes the calculation of the change of a feature amount in Example Variation 2.

In the growth model 131 shown in FIG. 13, if the area of the first leaf in the reference plant model increases by +10.0 [mm], the Q factor of the reference resonance frequency fc1 changes by Qsub3. In view of this, +10.0 [mm], which indicates the change of the area of the leaf, is stored as "area" under "change parameter", which is a state of the first leaf, and Qsub3, which indicates the change of the Q factor, is stored as "fc1 Q factor change" under "change information", and these values are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "area" and the like), and such change information is stored as shown in the growth model 131 shown in FIG. 13.

The following describes plant state estimation in Example Variation 2.

The collection unit 303 collects, from the vibrometer 301a, vibration information indicating vibration generated by the first leaf and the second leaf actually rubbing against each other. Specifically, first, the collection unit 303 collects vibration information from the vibrometer 301a in a time series, and stores the vibration information in a storage unit (not shown).

Next, using the collected vibration information, the extraction unit 304 generates a frequency response regarding the vibration of the first leaf, and extracts feature amounts of the first leaf from the generated frequency response.

Next, the calculation unit 305 calculates change, which indicates growth of the first leaf, based on the feature amount of the first leaf that was extracted by the extraction unit 304 and a reference feature amount of the first leaf. The calculation unit 305 then generates change information using the calculated change of the first leaf, and stores the change information in the storage unit.

Alternatively, instead of using the plant model, the calculation unit 305 may use feature information of the first leaf that was actually measured in the reference state as the reference feature amount, and calculate the difference (change) between that reference feature amount and a feature amount in the feature information acquired from the extraction unit 304.

Next, using the change information generated by the calculation unit 305, the estimation unit 306 references the growth model 131 and estimates a state of the first leaf.

Next, the growth information generation unit 307 generates growth information in which the state of the first leaf estimated by the estimation unit 306 and a time indicating the time at which the vibration information was measured are associated with each other. The growth information generation unit 307 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 308 then uses the growth information to generate outputtable output information in order to output the growth information to the output device 203. Thereafter, the output information generation unit 308 outputs the output information to the output device 203.

[Effects of Example Variation 2]

As described above, according to the plant state estimation unit 300, it is possible to extract a feature amount regarding a frequency response from the vibration of a leaf of a target plant, calculate the difference (change) between a reference feature amount and the extracted feature amount, and estimate a plant state (plant growth state) based on the calculated change of the feature amount.

[Example Variation 3]

The following describes Example Variation 3. In Example Variation 3, fruit growth can be estimated more precisely than in Example Variation 1. The following describes the configuration of a plant state estimation unit 300' in Example Variation 3 with reference to FIGS. 14 and 15.

Figure 14:
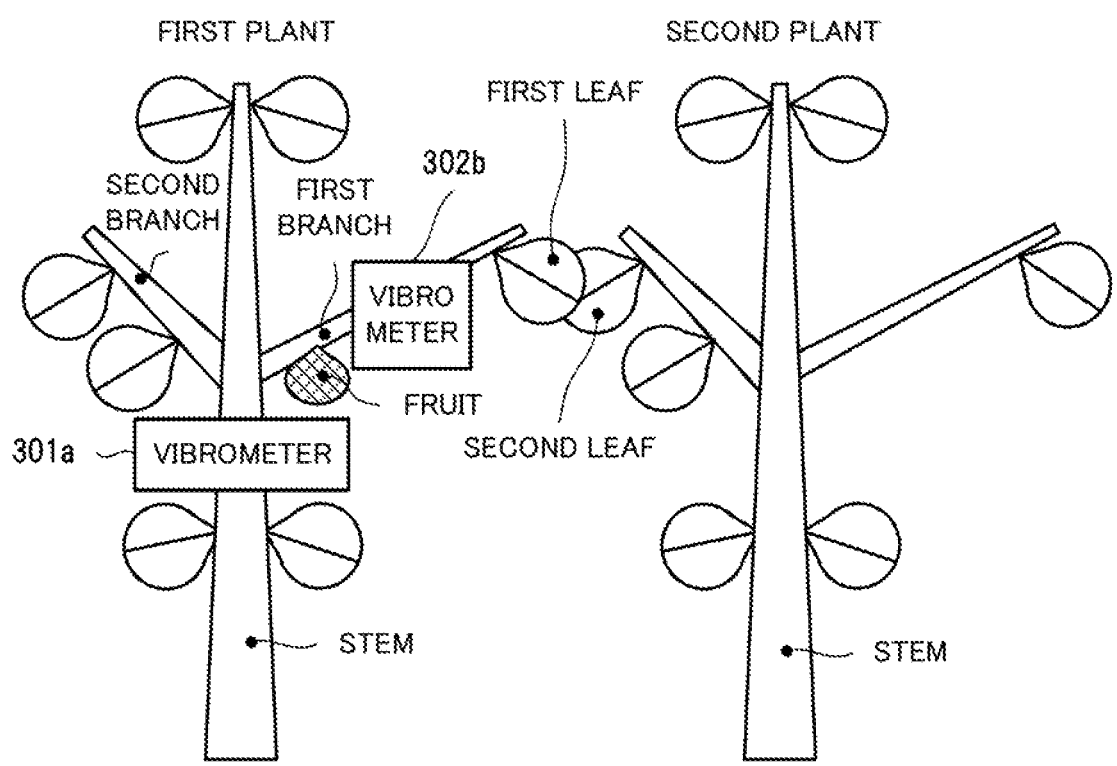
FIG. 14 is a diagram for describing the estimation of the state of a fruit.
Figure 15:
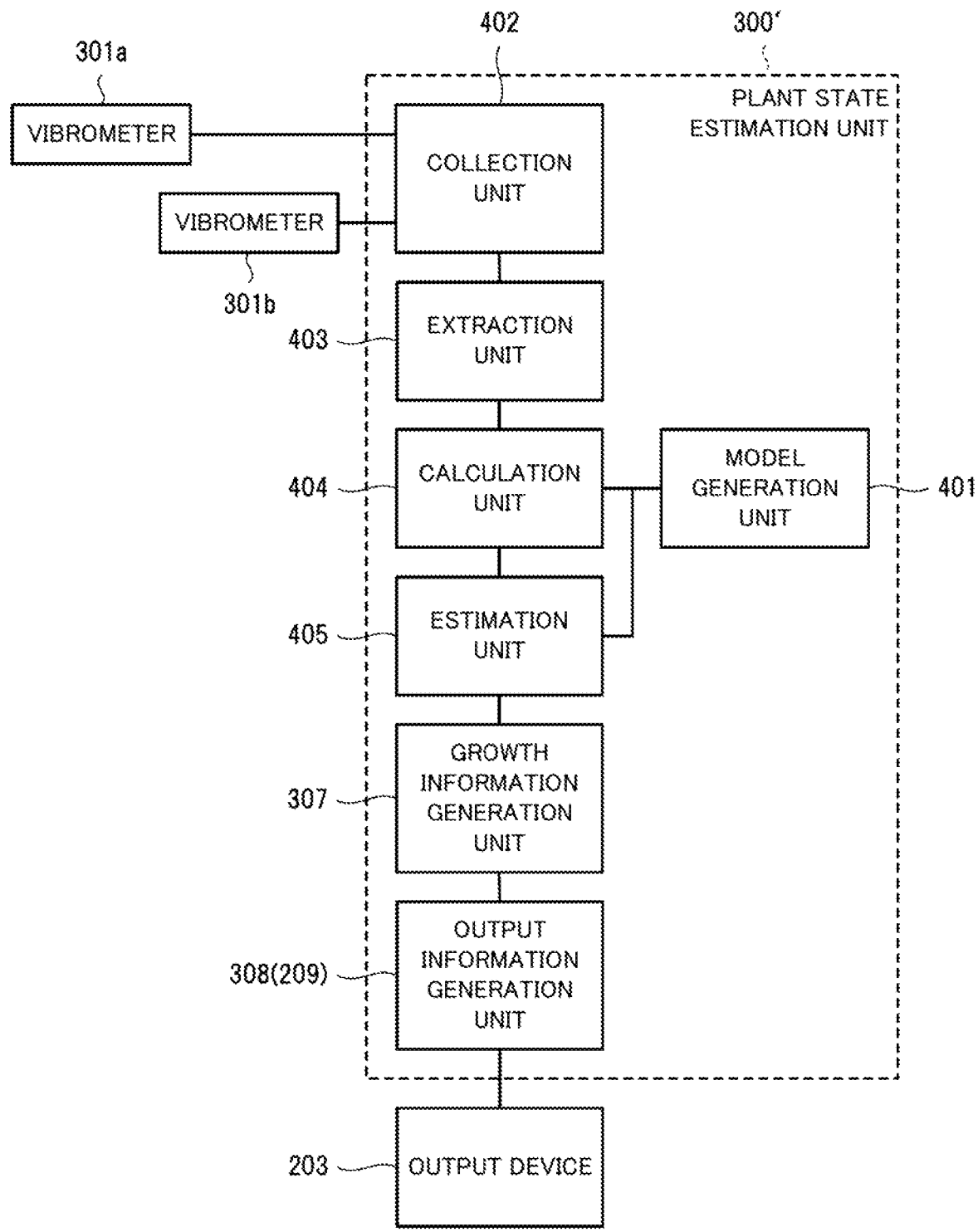
FIG. 15 is a diagram showing an example of a plant state estimation unit in Example Variation 3.

FIG. 14 is a diagram for describing the estimation of the state of a fruit. FIG. 15 is a diagram showing an example of a plant state estimation unit in Example Variation 3. As shown in FIG. 14, in Example Variation 3, if a fruit is growing on a first branch, vibration of the first branch is measured using vibrometers 301a and 301b.

As shown in FIG. 15, in the Example Variation 3, the plant state estimation unit 300' includes a model generation unit 401, a collection unit 402, an extraction unit 403, a calculation unit 404, an estimation unit 405, the growth information generation unit 307, and the output information generation unit 308.

First, the plant state estimation unit 300' uses vibration of the target plant measured at different locations (vibrometers 301a and 301b) to calculate a transfer function, and extracts a feature amount in a frequency response of the transfer function. Based on the extracted feature amount and a reference feature amount generated based on a frequency response of a reference transfer function, the plant state estimation unit 300' calculates change that indicates growth of the plant. The plant state estimation unit 300' then estimates a plant state by, with use of the calculated change, referencing state information in which changes of feature amounts from reference feature amounts corresponding to plant growth are associated with plant states. Next, the plant state estimation unit 300' outputs the estimated plant state to the output device 203 for presentation to the user.

The plant state estimation unit 300' will be described in detail below.

The model generation unit 401 executes a growth model simulation on a target plant in order to generate a growth model of the target plant, and stores the growth model in a storage unit (not shown). The storage unit that stores the growth model may be provided in the plant monitoring apparatus 100, or may be provided outside the plant monitoring apparatus 100.

The growth model simulation is for calculating a feature amount of the target plant in a reference state (reference feature amount) and a feature amount that changes along with growth (growth feature amount), associating change in the growth feature amount relative to the calculated reference feature amount with a plant state, and storing the result as a growth model.

Here, assuming that estimation of the growth state of the target plant is performed at a time t0, the reference state is a state of the target plant at a time that is at least before the time t0.

The following describes feature amount calculation in the growth model simulation.

(a1") First, the model generation unit 401 models the target plant in order to generate plant models. The model generation unit 401 generates a plant model for the reference state and various possible states of growth of the target plant after the reference state. In the example shown in FIG. 15, the various possible states of growth are various possible states that a fruit on the first branch can take while growing. Also, the plant model is obtained with use of a numerical model that uses a finite element method or a mathematical model that uses a mathematical expression, for example.

(a2') Next, the model generation unit 401 applies vibration to some or all of the generated plant models (including the reference state) by virtually applying pre-set vibration for a pre-set time. The model generation unit 401 then measures the vibration and generates vibration information. Note that it is desirable that vibration in the plant model is measured at positions that correspond to the positions on the target plant where vibration is actually measured by the vibrometers 301a and 301b in the example in FIG. 15. It should be noted that the positions where vibration is measured in the plant model are not required to be the same as the positions on the target plant where the vibrometers 301a and 301b perform measurement.

(a3") Next, the model generation unit 401 calculates a transfer function $G(s)=Y(s)/X(s)=L(y(t))/L(x(t))$ for each of the generated plant models, where a signal x(t) is information corresponding to the vibration information measured by the vibrometer 301a, and a signal y(t) is information corresponding to the vibration information measured by the vibrometer 301b. The model generation unit 401 then generates frequency response information using the frequency responses expressed by the transfer function G(s) as shown in FIG. 16.

FIG. 16 is a diagram for describing the frequency responses and the resonance frequencies of transfer functions of plant models. A graph 161 in FIG. 16 shows the frequency response of a plant model in the reference state. A graph 162 shows the frequency response of a plant model in the case where a portion of the target plant has grown.

(a4") Next, using the frequency responses of the generated plant models, the model generation unit 401 extracts, as the feature amount, either the resonance frequency or a value indicating how damped the resonance frequency is (Q factor), or both of them, from the frequency response. It should be noted that the feature amount is not limited to being the resonance frequency or the Q factor.

The graph 161 in FIG. 16 shows resonance frequencies fc11, fc22, and fc33. The graph 162 shows that the resonance frequency fc3 changes to fc3" in accordance with growth of the portion.

(a5") Next, the model generation unit 401 generates plant model feature information for each plant model by associating identification information that identifies the plant model, the states of portions of the plant model, and one or more feature amounts with each other. Note that the states of portions refers to information indicating states of the fruit or the like.

(a6") Next, the model generation unit 401 calculates the difference (change) between a feature amount that corresponds to the plant model feature information for the reference state (reference feature amount) and a feature amount that corresponds to the plant model feature information for a state of growth after the reference state (growth feature amount).

(a7") Next, the model generation unit 401 generates a growth model for each plant model as shown in FIG. 17 by associating the states of portions of the plant model, change parameters indicating change of portions of the plant model, and the changes of one or more feature amounts corresponding to the change parameters with each other, and stores the growth models in the storage unit.

FIG. 17 is a diagram showing an example of the data structure of a growth model. In a growth model 171 shown in FIG. 17, "portion", which indicates a portion of the plant model, "change parameter", which indicates states of the portion of the plant model, and "change information", which indicates change in the growth feature amounts corresponding to the reference feature amounts, are associated with each other.

The following describes the calculation of the change of feature amounts.

For example, as shown in FIG. 16, the resonance frequencies fc11, fc22, fc33 and so on are extracted in the reference plant model, and in the plant model where the fruit has grown in the reference plant model, a resonance frequency occurs at the frequency fc3", which is different from the resonance frequency fc3, as shown in the graph 162 in FIG. 16.

In such a case, if the fruit weight in the reference plant model has changed by +0.5 [kg] as in the first row of the growth model shown in FIG. 17 for example, the resonance frequency fc3" appears at a position that is shifted by +0.3 [Hz] from the resonance frequency fc33. In view of this, +0.5 [kg], which indicates the change of the fruit weight, which is a state of the plant ("weight" under "change parameter"), and +0.3 [Hz], which indicates the change of the resonance frequency in the "change information" ("fc3 change"), are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "weight" and the like), and such change information is stored as shown in the growth model 171 shown in FIG. 17.

The following describes the estimation of plant states.

The collection unit 402 collects vibration information from the vibrometers 301a and 301b in the case where the state of the target plant is to actually be estimated. Specifically, first, the collection unit 402 collects vibration information from the vibrometers 301a and 301b in a time series, and stores the vibration information in a storage unit (not shown). The storage unit may be provided in the plant monitoring apparatus 100, or may be provided outside the plant monitoring apparatus 100.

The extraction unit 403 calculates the transfer function with use of the vibration information collected by the vibrometers 301a and 301b, and extracts feature amounts from the frequency response of the calculated transfer function.

(b1") The extraction unit 403 acquires, from the aforementioned storage unit, vibration information corresponding to a pre-set duration at a pre-set interval. Here, the set interval and the set duration can be set as desired by the user.

(b2") Next, the extraction unit 403 calculates a transfer function $G(s)=Y(s)/X(s)=L(y(t))/L(x(t))$, where a signal x(t) is information corresponding to the vibration information measured by the vibrometer 301a, and a signal y(t) is information corresponding to the vibration information measured by the vibrometer 301b. The extraction unit 403 then generates frequency response information using the frequency responses expressed by the transfer function G(s).

(b3") Next, the extraction unit 403 extracts a feature amount from the generated frequency response. The extraction unit 403 extracts a resonance frequency or a value indicating how damped the resonance frequency is (Q factor), or both, from the frequency response. It should be noted that the feature amount is not limited to being the resonance frequency or the Q factor.

The calculation unit 404 then calculates change, which indicates plant growth, based on the feature amount that was extracted by the extraction unit 403 and a reference feature amount.

(c1") First, the calculation unit 404 acquires feature information from the extraction unit 403. The calculation unit 404 also acquires plant model feature information for the reference state from the growth model.

(c2") Next, the calculation unit 404 calculates the difference (change) between a reference feature amount in the plant model feature information for the reference state and a feature amount in the feature information that was acquired from the extraction unit 403. The calculation unit 404 generates change information 181 that indicates the change of the feature amount as shown in FIG. 18 for example, and stores the change information 181 in the storage unit. FIG. 18 is a diagram showing an example of the data structure of change information.

Alternatively, instead of using the plant model, the calculation unit 404 may use feature information of the target plant that was actually measured in the reference state as the reference feature amount, and calculate the difference (change) between that reference feature amount and a feature amount in the feature information acquired from the extraction unit 403.

Then, using the calculated change information, the estimation unit 405 estimates the state of the plant by referencing the growth model, finding change information in the growth model that is similar to the calculated change information, and selecting a plant state that corresponds to the found change information.

(d1") Using the change information 181 shown in FIG. 18 that was calculated by the calculation unit 404, the estimation unit 405 references the growth model 171 shown in FIG. 17 and extracts change information that is similar to the change information 181.

(d2") Next, the estimation unit 405 selects the "change parameter" that is associated with the extracted change information 181, and estimates the growth of the portion of the plant indicated by the "change parameter" as the plant state. The change information 181 is similar to the change information in the first row in the growth model 171, and therefore the estimation unit 405 selects "fruit weight+0.5 [kg]" as the plant state.

The growth information generation unit 307 generates growth information by associating the plant portion state estimated by the estimation unit 405 with a time that indicates the time at which the vibration information was measured. The growth information generation unit 307 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 308 then uses the growth information to generate output information that is to be used for outputting the growth information to the output device 203. Thereafter, the output information generation unit 308 outputs the output information to the output device 203.

[Effects of Example Variation 3]

As described above, according to the plant state estimation unit 300', it is possible to extract a feature amount regarding a transfer function from the vibration of a portion of a target plant, calculate the difference (change) between a reference feature amount and the extracted feature amount, and estimate the state of a fruit or the like of the plant (fruit growth state) based on the calculated change of the feature amount.

[Apparatus Operation]

Figure 19:
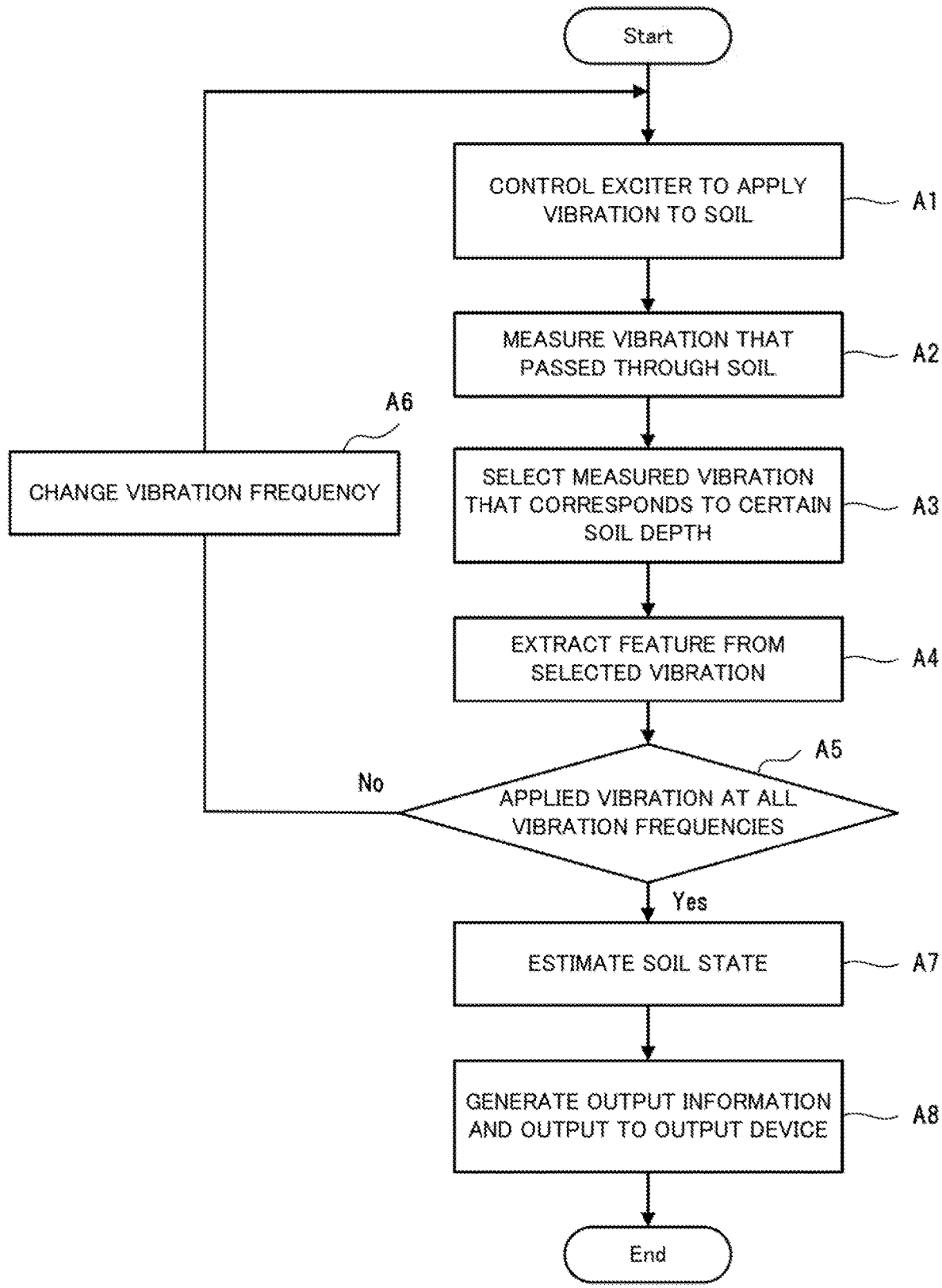
FIG. 19 is a diagram showing an example of operations of a soil state estimation unit.

Operations of the soil state estimation unit 200 will be described in detail below. The following describes operations of the soil state estimation unit 200 according to the example embodiment of the present invention with reference to FIG. 19. FIG. 19 is a diagram showing an example of operations of the soil state estimation unit. The following description references FIGS. 2 and 4 to 6 when appropriate. Also, in the present example embodiment, a soil state estimation method is carried out by causing the soil state estimation unit 200 to operate. Accordingly, the following description of operations of the soil state estimation unit 200 will substitute for a description of a soil state estimation method.

The following describes the case where the vibration frequency is swept when estimating the soil state, with reference to FIG. 19.

In step A1, first, the control unit 204 controls the exciter 201 so as to apply vibration to the soil. Specifically, in step A1, the control unit 204 transmits, to the exciter 201, vibration setting information that is used in order to set the vibration strength and the vibration frequency. Thereafter, the exciter 201 produces vibration in the soil based on the received vibration setting information.

Next, in step A2, the collection unit 205 collects vibration information regarding vibration that passed through the soil and was measured by the vibrometer 202. Specifically, in step A2, first, the collection unit 205 collects vibration information from the vibrometer 202 in a time series. The collection unit 205 then outputs the collected vibration information to the selection unit 206. The collection unit 205 also stores the vibration information in a storage unit (not shown).

Next, in step A3, using the transmission time for which vibration passed through the soil, the selection unit 206 selects vibration that was measured via the soil at a certain soil depth. Specifically, in step A3, based on the transmission time of vibration that corresponds to the target soil depth (soil layer), the selection unit 206 selects vibration information that corresponds to the target soil layer from the vibration information that was collected by the collection unit 205.

Specifically, in step A3, first, the selection unit 206 acquires vibration information from the collection unit 205. Next, the selection unit 206 calculates a selected time based on the transmission time that corresponds to the target soil layer. For example, in the case of selecting vibration information that corresponds to the soil layer 1, using the transmission time T1 that corresponds to the soil layer 1, the selected time is calculated as the duration from when vibration is produced by the exciter 201 in the soil until when vibration 1 reflected by the soil layer 1 is measured by the vibrometer 202.

Next, using the selected time, the selection unit 206 selects vibration information that corresponds to the target soil layer from the acquired vibration information. Specifically, the selection unit 206 selects the vibration information that was measured in the selected time that corresponds to the target soil layer.

Note that letting the transmission time T1 be expressed by a time te1 at which vibration produced in the soil surface at a time t0 is measured at the soil surface after passing through the soil layer 1, a selected time ts1 corresponding to the soil layer 1 is the duration from a time before the time te1 (te1-a1) until when vibration reflected by the soil layer 1 is no longer measured (te1+b1).

Also, the time a1 (start information) and the time b1 (end information) are obtained by experimentation, simulation, or the like. Also, selected times ts2, ts3, and so on for the other soil layers 2, 3, and so on are calculated similarly to the case of the soil layer 1.

Note that the above-described transmission time, start information, and end information for each soil layer are stored in advance in a storage unit in association with the corresponding soil layers, as shown in selected time generation information 41 shown in FIG. 4, for example.

Alternatively, soil layers and selected times may be stored in association with each other in the storage unit in advance, as shown in selected time generation information 42 in FIG. 4.

Next, in step A4, the extraction unit 207 extracts a feature, which indicates a vibration feature, for the vibration of each selected time. One conceivable example of a vibration feature is a resonance frequency.

Specifically, in step A4, first, the extraction unit 207 acquires reference vibration information (input value x(t)), which is reference information that corresponds to vibration produced in the soil by the exciter 201, and vibration information (output value y(t)) that corresponds to the soil layer selected by the selection unit 206.

The reference vibration information is obtained by experimentation, simulation, or the like, and is stored in the storage unit. Alternatively, the reference vibration information may be generated based on soil vibration that is measured by the vibrometer 202 and another vibrometer immediately after being produced.

Next, in step A4, the extraction unit 207 calculates a function that expresses the relationship between the input value x(t) and the output value y(t) that corresponds to the input value x(t). For example, a transfer function G(s) is calculated.

The input value x(t) and the output value y(t) are subjected to Laplacian conversion, and the transfer function G(s) is expressed by the ratio (Y(s)/X(s)) between the resulting input value X(s) and output value Y(s). Here, the ratio expresses how the vibration was transmitted through the soil.

Next, in step A4, using the relationship between the frequency (sweeped frequency) and the ratio (amplitude) that correspond to the vibration, the extraction unit 207 extracts the frequency that corresponds to the peak of the ratio as the vibration feature (resonance frequency). For example, as shown in FIG. 5, the frequency that corresponds to the peak of the ratio (amplitude) is the resonance frequency.

Note that the reason for using the resonance frequency is that because the resonance frequency changes according to the soil state, the soil state can be estimated with use of the relationship between soil states and resonance frequencies.

Note that the vibration feature is not limited to being obtained by the above-described method, and may be a vibration feature other than the resonance frequency.

Next, in step A5, the control unit 204 determines whether or not the exciter 201 has been caused to vibrate at all of the vibration frequencies that were set in advance. If the exciter 201 has vibrated at all of the vibration frequencies (step A5: Yes), processing for estimating the soil state is executed in step A7. If there is a vibration frequency for which vibration has not been executed (step A5: No), the control unit 204 changes the vibration frequency in step A6. In other words, the current vibration frequency is changed in order to sweep the vibration frequency.

Next, in step A7, using the feature, the estimation unit 208 references the soil estimation information in which features and soil states are associated with each other, and estimates the soil state. Specifically, in step A7, first, the estimation unit 208 acquires the feature from the extraction unit 207. Next, using the acquired feature, the estimation unit 208 references the soil estimation information in which features and soil states are associated with each other, and estimates the soil state. The soil estimation information is stored in the storage unit (not shown) in advance, for example.

The soil estimation information is information in which soil hardness [$kg/m^2$], soil root quantity [$m/m^3$], soil moisture content [%], soil composition, or any combination thereof is associated with a feature (e.g., resonance frequency [Hz]). Note that the soil states are not limited to the information described above.

Next, in step A8, the output information generation unit 209 generates output information with use of the estimated soil state, and outputs the output information to the output device 203.

Specifically, in step A8, first, the output information generation unit 209 acquires information indicating the soil state from the estimation unit 208. Next, using the selected soil layer and the soil state that corresponds to that soil layer, the output information generation unit 209 generates output information for causing the output device 203 to output the soil state that corresponds to the soil layer. The output information generation unit 209 then outputs the generated output information to the output device 203, and causes the output device 203 to output the soil state that corresponds to the soil layer.

Operations of the plant state estimation unit 300 will be described in detail below.

Figure 20:
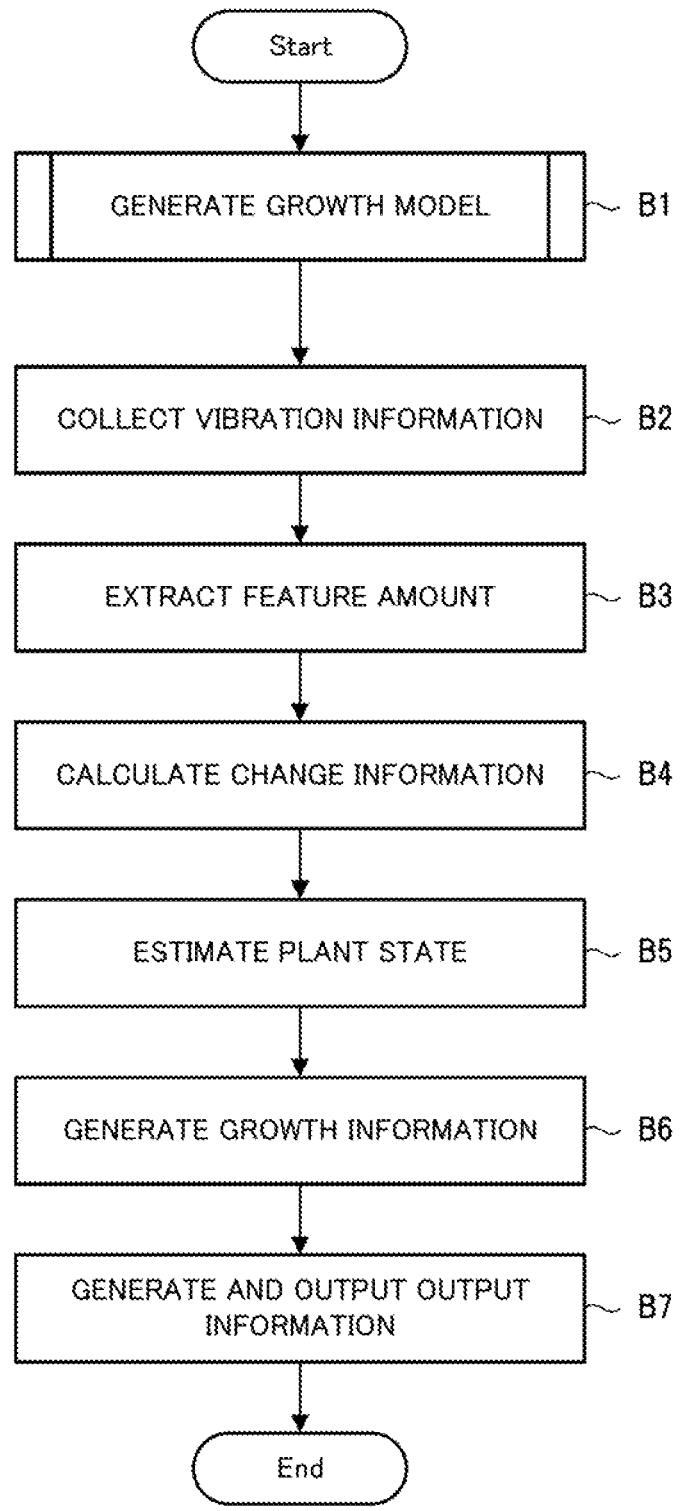
FIG. 20 is a diagram showing an example of operations of the plant state estimation unit.
Figure 21:
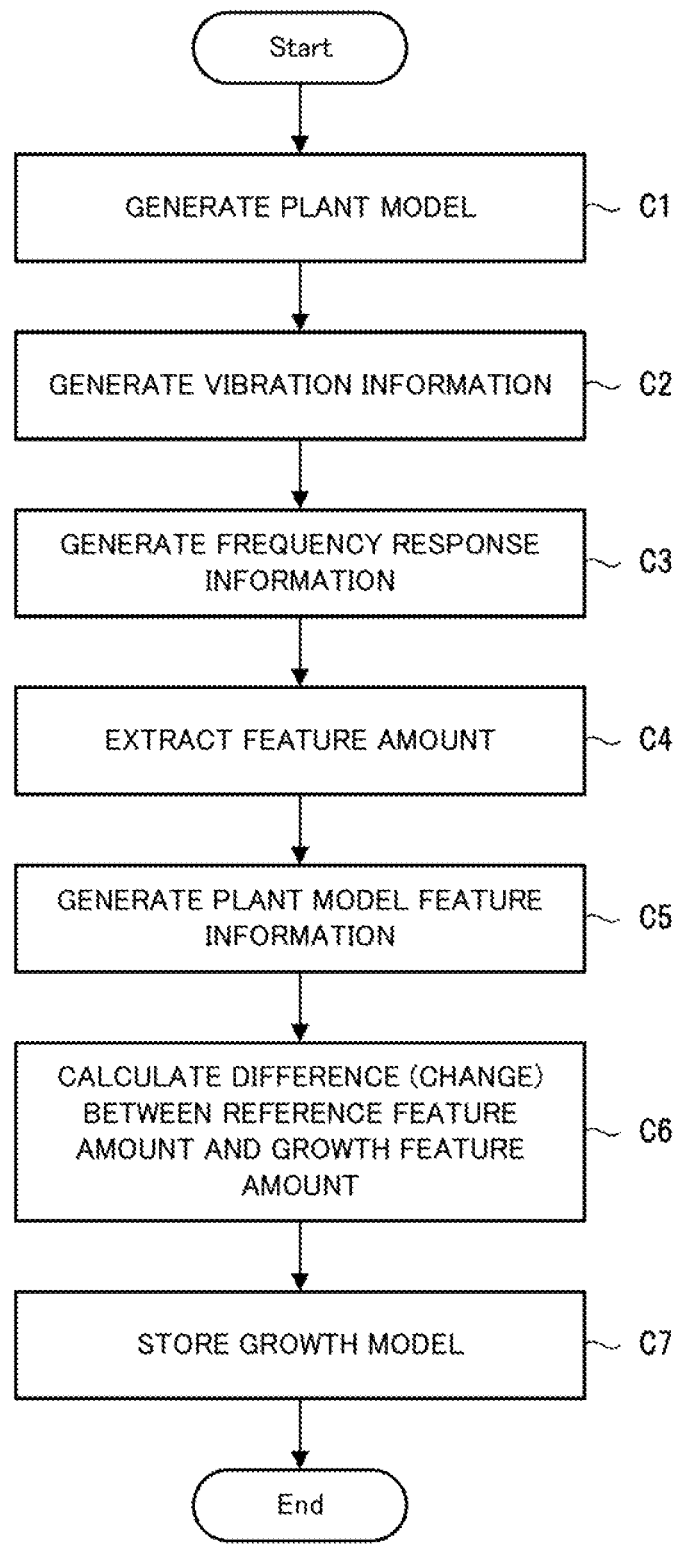
FIG. 21 is a diagram showing an example of operations of a model generation unit.

The following describes operations of the plant state estimation unit 300 according to the example embodiment of the present invention with reference to FIGS. 20 and 21. FIG. 20 is a diagram showing an example of operations of the plant state estimation unit. FIG. 21 is a diagram showing an example of operations of the model generation unit. The following description references FIGS. 3 and 7 to 13 when appropriate. Also, in the present example embodiment, a plant state estimation method is carried out by causing the plant state estimation unit 300 to operate. Accordingly, the following description of operations of the plant state estimation unit 300 will substitute for a description of a plant state estimation method.

The following describes growth model generation with reference to FIGS. 20 and 21.

In step B1 in FIG. 20, the model generation unit 302 generates state information (growth model) indicating states of the target plant. Step B1 will be described below in more detail with reference to FIG. 21.

In step C1 (a1) in FIG. 21, first, the model generation unit 302 models the target plant in order to generate plant models.

Next, in step C2 (a2), the model generation unit 302 applies vibration to some or all of the generated plant models (including the reference state) by virtually applying pre-set vibration for a pre-set time. The model generation unit 302 then measures the vibration and generates vibration information.

Next, in step C3 (a3), the model generation unit 302 converts the vibration information of the generated plant models from the time domain to the frequency domain (e.g., Fourier transform) in order to generate frequency response information that indicates frequency responses as shown in FIG. 7.

Next, in step C4 (a4), using the frequency responses of the generated plant models, the model generation unit 302 extracts, as the feature amount, either the resonance frequency or a value indicating how damped the resonance frequency is (Q factor), or both of them, from the frequency response. It should be noted that the feature amount is not limited to being the resonance frequency or the Q factor.

Next, in step C5 (a5), the model generation unit 302 generates plant model feature information for each plant model by associating identification information that identifies the plant model, the states of portions of the plant model, and one or more feature amounts with each other.

Next, in step C6 (a6), the model generation unit 302 calculates the difference (change) between a feature amount that corresponds to the plant model feature information for the reference state (reference feature amount) and a feature amount that corresponds to the plant model feature information for a state of growth after the reference state (growth feature amount).

Next, in step C7 (a7), the model generation unit 302 generates a growth model for each plant model as shown in FIG. 8 by associating the states of portions of the plant model, change parameters indicating change of portions of the plant model, and the changes of one or more feature amounts corresponding to the change parameters with each other, and stores the growth models in the storage unit.

Note that the model generation unit 302 may be provided separately from the plant monitoring apparatus 100. In this case, the system is configured such that the plant monitoring apparatus 100 and the model generation unit 302 can communicate with each other.

The following describes the estimation of plant states with reference to FIG. 20.

In step B2, the collection unit 303 collects vibration information from the vibrometers 301 (301a, 301b, or both) in the case where the state of the target plant is to actually be estimated. Specifically, in step B2, first, the collection unit 303 collects vibration information from the vibrometers 301 in a time series, and stores the vibration information in a storage unit (not shown). The storage unit may be provided in the plant monitoring apparatus 100, or may be provided outside the plant monitoring apparatus 100.

In step B3, the extraction unit 304 uses the vibration information, which indicates vibration of the target plant, to generate a frequency response regarding the vibration, and extracts feature amounts from the generated frequency response. In step B3, the following processing from (b1) to (b3) is performed.

(b1) In step B3, first, the extraction unit 304 acquires, from the aforementioned storage unit, vibration information corresponding to a pre-set duration at a pre-set interval. Here, the set interval and the set duration can be set as desired by the user.

(b2) Next, in step B3, the extraction unit 304 converts the vibration information collected over the pre-set duration from the time domain to the frequency domain (e.g., Fourier transform) to generate frequency response information that indicates the frequency response.

(b3) Next, in step B3, using the generated frequency responses, the extraction unit 304 extracts, as the feature amount, either the resonance frequency or a value indicating how damped the resonance frequency is (Q factor), or both of them, from the frequency response. It should be noted that the feature amount is not limited to being the resonance frequency or the Q factor.

In step B4, the calculation unit 305 then calculates change, which indicates plant growth, based on the feature amount that was extracted by the extraction unit 304 and a reference feature amount. In step B4, the following processing from (c1) to (c2) is performed.

(c1) In step B4, first, the calculation unit 305 acquires feature information from the extraction unit 304. The calculation unit 305 also acquires plant model feature information for the reference state from the growth model.

(c2) Next, in step B4, the calculation unit 305 calculates the difference (change) between a reference feature amount in the plant model feature information for the reference state and a feature amount in the feature information that was acquired from the extraction unit 304.

Alternatively, instead of using the plant model, the calculation unit 305 may use feature information of the target plant that was actually measured in the reference state as the reference feature amount, and calculate the difference (change) between that reference feature amount and a feature amount in the feature information acquired from the extraction unit 304.

In step B5, using the calculated change information, the estimation unit 306 estimates the state of the plant by referencing the growth model, finding change information in the growth model that is similar to the calculated change information, and selecting a plant state that corresponds to the found change information. In step B5, the following processing from (d1) to (d2) is performed.

(d1) In step B5, first, using the change information 91 shown in FIG. 9 that was calculated by the calculation unit 305, the estimation unit 306 references the growth model 81 shown in FIG. 8 and extracts change information that is similar to the change information 91.

(d2) Next, in step B5, the estimation unit 306 selects the "change parameter" that is associated with the extracted change information 91, and estimates the plant growth indicated by the "change parameter" as the plant state.

Next, in step B6, the growth information generation unit 307 generates growth information by associating the plant state estimated by the estimation unit 306 with a time that indicates the time at which the vibration information was measured.

Next, in step B7, the output information generation unit 308 then uses the growth information to generate outputtable output information in order to output the growth information to the output device 203. Thereafter, the output information generation unit 308 outputs the output information to the output device 203.

[Example Variation 1]

The following describes operations in Example Variation 1. In Example Variation 1, the portion of the target plant is a branch instead of the stem.

The following describes growth model generation in Example Variation 1

In Example Variation 1, in step B1 in FIG. 20 (steps C1 to C7 in FIG. 21), the model generation unit 302 executes growth model simulation on the first branch shown in FIG. 10 as the portion of the target plant, for example, in order to generate a growth model 111 that corresponds to the first branch of the target plant as shown in FIG. 11, and stores the growth model 111 in the storage unit (not shown).

The following describes plant state estimation in Example Variation 1 with reference to FIG. 20.

In step B2, the collection unit 303 collects vibration information indicating vibration of the first branch from the vibrometer 301b. Specifically, first, the collection unit 303 collects vibration information from the vibrometer 301b in a time series, and stores the vibration information in a storage unit (not shown).

Next, in step B3, using the vibration information that indicates vibration of the first branch, the extraction unit 304 generates a frequency response regarding the vibration of the first branch, and extracts a feature amount of the first branch from the generated frequency response.

Next, in step B4, the calculation unit 305 calculates change, which indicates growth of the first branch, based on the feature amount of the first branch that was extracted by the extraction unit 304 and a reference feature amount of the first branch. The calculation unit 305 then generates change information using the calculated change of the first branch, and stores the change information in the storage unit.

Alternatively, instead of using the plant model, the calculation unit 305 may use feature information of the first branch that was actually measured in the reference state as the reference feature amount, and calculate the difference (change) between that reference feature amount and a feature amount in the feature information acquired from the extraction unit 304.

Next, in step B5, using the change information generated by the calculation unit 305, the estimation unit 306 references the growth model 111 and estimates a state of the first branch.

Next, in step B6, the growth information generation unit 307 generates growth information by associating the first branch state estimated by the estimation unit 306 with a time that indicates the time at which the vibration information was measured. The growth information generation unit 307 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

Next, in step B7, the output information generation unit 308 then uses the growth information to generate outputtable output information in order to output the growth information to the output device 203. Thereafter, the output information generation unit 308 outputs the output information to the output device 203.

[Example Variation 2]

The following describes operations in Example Variation 2. In Example Variation 2, the portion of the target plant is a leaf. Specifically, in Example Variation 2, vibration generated when leaves rub against each other due to an external force is measured, and leaf growth is estimated using the measured vibration.

The following describes growth model generation in Example Variation 2 with reference to FIGS. 20 and 21.

In step B1 in FIG. 20, the model generation unit 302 generates state information (growth model) indicating states of the target plant. Step B1 will be described below in more detail with reference to FIG. 21.

In the Example Variation 2, in step C1 (a1') in FIG. 21, first, the model generation unit 302 generates plant models for the first plant and the second plant in the example shown in FIG. 12. The plant models for the first plant and the second plant are generated for a reference state and various states of change in the process of growth of the first plant and the second plant. Note that leaf overlap is not limited to the overlapping of two leaves.

Next, in step C2 (a2'), the model generation unit 302 virtually applies pre-set vibration for a pre-set time to the various plant models generated using the first plant and second plant, in order to apply vibration caused by the first leaf and the second leaf rubbing against each other. The model generation unit 302 then measures the vibration and generates vibration information. Note that it is desirable that vibration is measured at a position that corresponds to the position on the target plant where vibration is actually measured by the vibrometer 301a.

Next, in step C3 (a3'), the model generation unit 302 converts the vibration information of the various plant models generated using the first plant and the second plant from the time domain to the frequency domain (e.g., Fourier transform) in order to generate frequency response information that indicates frequency responses.

Next, in step C4 (a4'), using the frequency responses of the generated plant models, the model generation unit 302 extracts, as the feature amount, either the resonance frequency or a value indicating how damped the resonance frequency is (Q factor), or both of them, from the frequency response. It should be noted that the feature amount is not limited to being the resonance frequency or the Q factor.

Next, in step C5 (a5'), the model generation unit 302 generates plant model feature information for the area of the first leaf for each plant model by associating identification information that identifies the plant model, the states of the first leaf of the plant model (change parameters), and one or more feature amounts with each other.

Next, in step C6 (a6'), the model generation unit 302 calculates the difference (change) between a feature amount that corresponds to the generated plant model feature information for the reference state (reference feature amount) and a feature amount that corresponds to the plant model feature information for a state of growth after the reference state (growth feature amount).

Next, in step C7 (a7'), the model generation unit 302 generates a growth model 131 shown in FIG. 13 for each plant model by associating the states of the first leaf of the plant model, change parameters indicating change of the first leaf of the plant model, and the changes of one or more feature amounts corresponding to the change parameters with each other, and stores the growth models 131 in the storage unit.

The following describes plant state estimation in Example Variation 2 with reference to FIG. 20.

In step B2, the collection unit 303 collects, from the vibrometer 301a in FIG. 12, vibration information indicating vibration generated by the first leaf and the second leaf rubbing against each other. Specifically, first, the collection unit 303 collects vibration information from the vibrometer 301a in a time series, and stores the vibration information in a storage unit (not shown).

Next, in step B3, using the collected vibration information, the extraction unit 304 generates a frequency response regarding the vibration of the first leaf, and extracts feature amounts of the first leaf from the generated frequency response.

Next, in step B4, the calculation unit 305 calculates change, which indicates growth of the first leaf, based on the feature amount of the first leaf that was extracted by the extraction unit 304 and a reference feature amount of the first leaf. The calculation unit 305 then generates change information using the calculated change of the first leaf, and stores the change information in the storage unit.

Alternatively, instead of using the plant model, the calculation unit 305 may use feature information of the first leaf that was actually measured in the reference state as the reference feature amount, and calculate the difference (change) between that reference feature amount and a feature amount in the feature information acquired from the extraction unit 304.

Next, in step B5, using the change information generated by the calculation unit 305, the estimation unit 306 references the growth model 131 and estimates a state of the first leaf.

Next, in step B6, the growth information generation unit 307 generates growth information by associating the first leaf state estimated by the estimation unit 306 with a time that indicates the time at which the vibration information was measured. The growth information generation unit 307 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

Next, in step B7, the output information generation unit 308 then uses the growth information to generate outputtable output information in order to output the growth information to the output device 203. Thereafter, the output information generation unit 308 outputs the output information to the output device 203.

[Example Variation 3]

Figure 22:
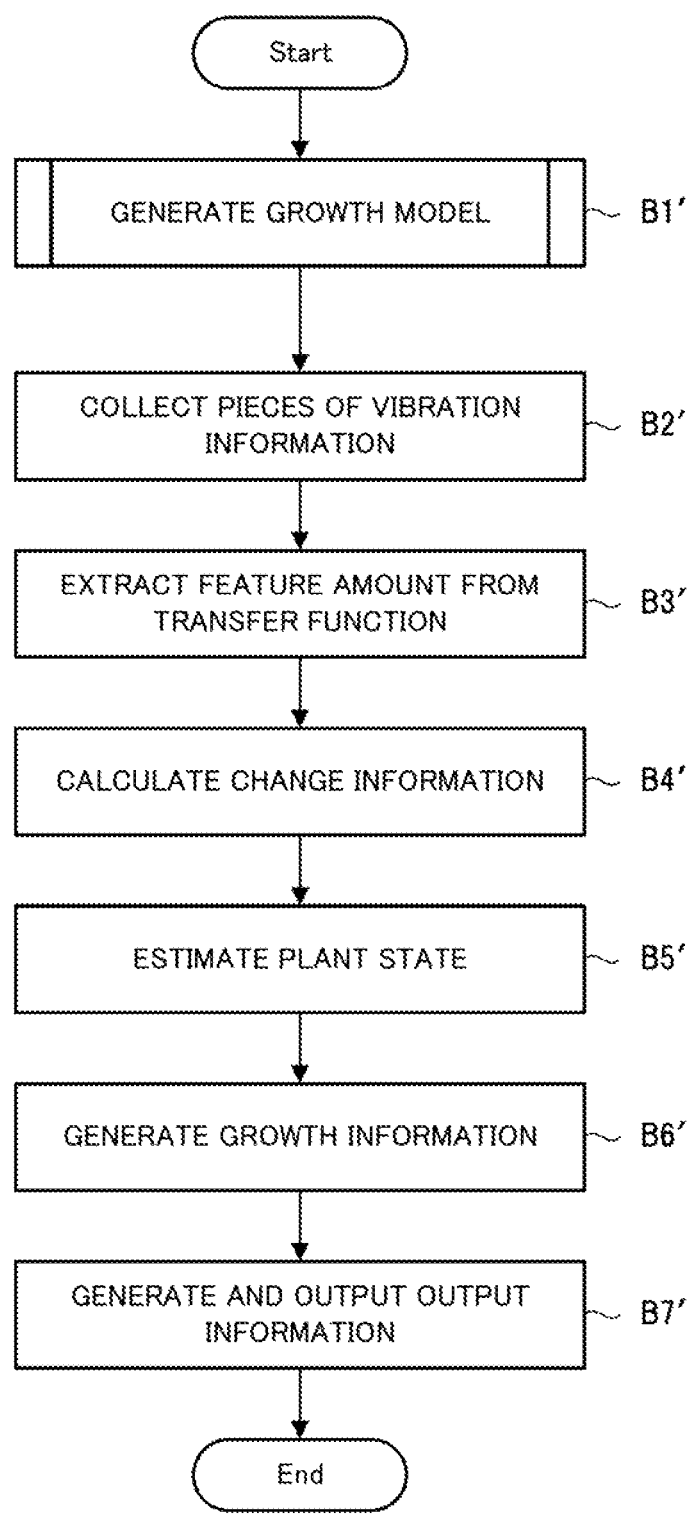
FIG. 22 is a diagram showing an example of operations of the plant state estimation unit.
Figure 23:
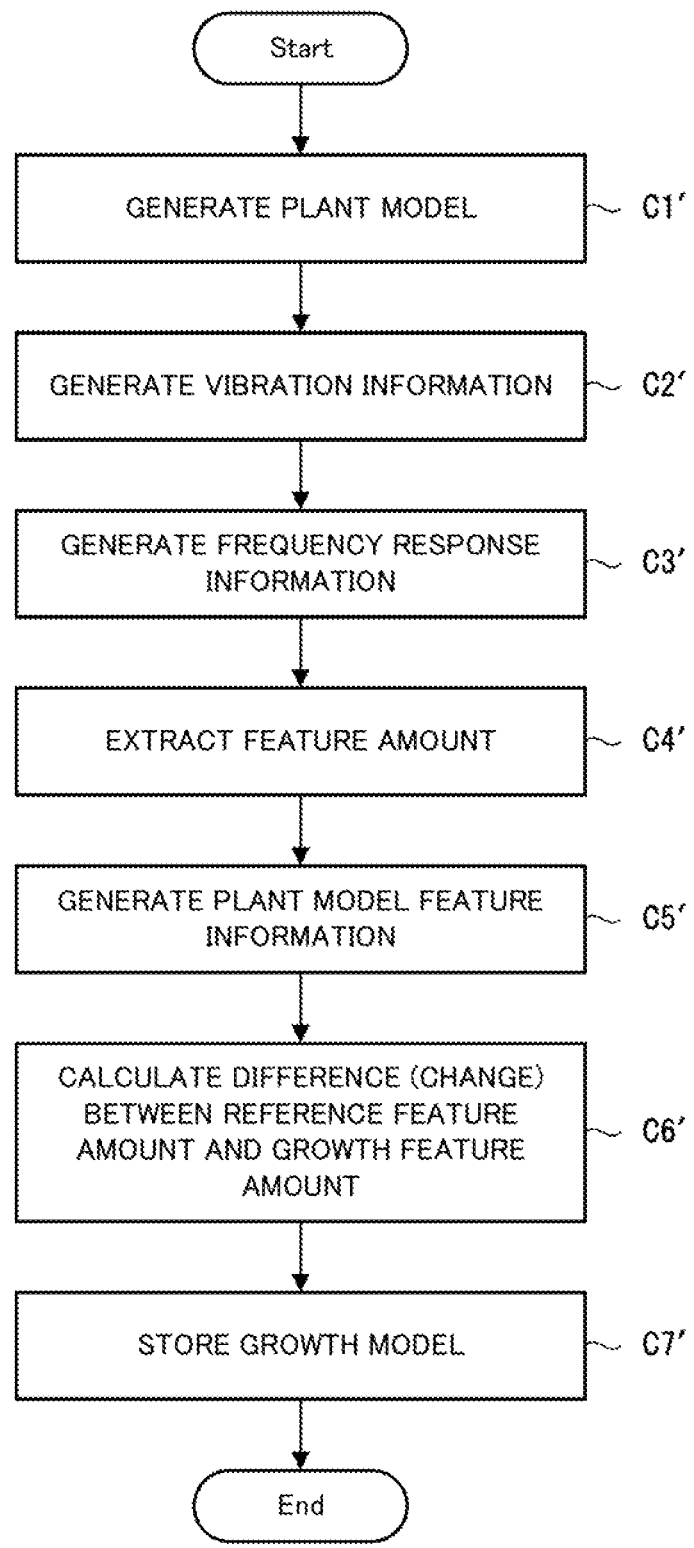
FIG. 23 is a diagram showing an example of operations of the model generation unit.

The following describes operations of the plant state estimation unit 300' according to the example embodiment of the present invention with reference to FIGS. 22 and 23. FIG. 22 is a diagram showing an example of operations of the plant state estimation unit. FIG. 23 is a diagram showing an example of operations of the model generation unit. The following description references FIGS. 14 to 18 when appropriate. Also, in the present example embodiment, a plant state estimation method is carried out by causing the plant state estimation unit 300' to operate. Accordingly, the following description of operations of the plant state estimation unit 300' will substitute for a description of a plant state estimation method.

The following describes growth model generation in Example Variation 3 with reference to FIGS. 22 and 23.

In step B1' in FIG. 22, the model generation unit 401 generates state information (growth model) indicating states of the target plant. Step B1' will be described below in more detail with reference to FIG. 23.

In step C1' (a1"), first, the model generation unit 401 models the target plant in order to generate plant models.

Next, in step C2' (a2"), the model generation unit 401 applies vibration to some or all of the generated plant models (including the reference state) by virtually applying pre-set vibration for a pre-set time. The model generation unit 401 then measures the vibration and generates vibration information. Note that it is desirable that vibration in the plant model is measured at positions that correspond to the positions on the target plant where vibration is actually measured by the vibrometers 301a and 301b in the example in FIG. 14. It should be noted that the positions where vibration is measured in the plant model are not required to be the same as the positions on the target plant where the vibrometers 301a and 301b perform measurement.

Next, in step C3' (a3") the model generation unit 401 calculates a transfer function $G(s)=Y(s)/X(s)=L(y(t))/L(x(t))$ for each of the generated plant models, where a signal $x(t)$ is information corresponding to the vibration information measured by the vibrometer 301a, and a signal $y(t)$ is information corresponding to the vibration information measured by the vibrometer 301b. The model generation unit 401 then generates frequency response information using the frequency responses expressed by the transfer function $G(s)$ as shown in FIG. 16.

Next, in step C4' (a4"), using the frequency responses of the generated plant models, the model generation unit 401 extracts, as the feature amount, either the resonance frequency or a value indicating how damped the resonance frequency is (Q factor), or both of them, from the frequency response. It should be noted that the feature amount is not limited to being the resonance frequency or the Q factor.

Next, in step C5' (a5"), the model generation unit 401 generates plant model feature information for each plant model by associating identification information that identifies the plant model, the states of portions of the plant model, and one or more feature amounts with each other. Note that the states of portions refers to information indicating states of the fruit or the like.

Next, in step C6' (a6"), the model generation unit 401 calculates the difference (change) between a feature amount that corresponds to the plant model feature information for the reference state (reference feature amount) and a feature amount that corresponds to the plant model feature information for a state of growth after the reference state (growth feature amount).

Next, in step C7' (a7"), the model generation unit 401 generates a growth model for each plant model as shown in FIG. 17 by associating the states of portions of the plant model, change parameters indicating change of portions of the plant model, and the changes of one or more feature amounts corresponding to the change parameters with each other, and stores the growth models in the storage unit.

The following describes the estimation of plant states with reference to FIG. 22.

In step B2' in FIG. 22, the collection unit 402 collects vibration information from the vibrometers 301a and 301b in the case where the state of the target plant is to actually be estimated. Specifically, in step B2', first, the collection unit 402 collects vibration information from the vibrometers 301a and 301b in a time series, and stores the vibration information in a storage unit (not shown). The storage unit may be provided in the plant monitoring apparatus 100, or may be provided outside the plant monitoring apparatus 100.

In step B3', the extraction unit 403 calculates the transfer function with use of the vibration information collected by the vibrometers 301a and 301b, and extracts feature amounts from the frequency response of the calculated transfer function. In step B3, the following processing from (b1") to (b3") is performed.

(b1") In step B3', first, the extraction unit 403 acquires, from the aforementioned storage unit, vibration information corresponding to a pre-set duration at a pre-set interval. Here, the set interval and the set duration can be set as desired by the user.

(b2") Next, in step B3', the extraction unit 403 calculates a transfer function $G''(s)=Y(s)/X(s)=L(y(t))/L(x(t))$, where a signal $x(t)$ is information corresponding to the vibration information measured by the vibrometer 301$a$, and a signal $y(t)$ is information corresponding to the vibration information measured by the vibrometer 301$b$. The extraction unit 403 then generates frequency response information using the frequency responses expressed by the transfer function $G(s)$.

(b3") Next, in step B3', the extraction unit 403 extracts a feature amount from the generated frequency response. The extraction unit 403 extracts a resonance frequency or a value indicating how damped the resonance frequency is (Q factor), or both, from the frequency response. It should be noted that the feature amount is not limited to being the resonance frequency or the Q factor.

In step B4', the calculation unit 404 then calculates change, which indicates plant growth, based on the feature amount that was extracted by the extraction unit 403 and a reference feature amount. In step B4', the following processing from (c1") to (c2") is performed.

(c1") In step B4', first, the calculation unit 404 acquires feature information from the extraction unit 403. The calculation unit 404 also acquires plant model feature information for the reference state from the growth model.

(c2") Next, in step B4', the calculation unit 404 calculates the difference (change) between a reference feature amount in the plant model feature information for the reference state and a feature amount in the feature information that was acquired from the extraction unit 403.

Alternatively, instead of using the plant model, the calculation unit 404 may use feature information of the target plant that was actually measured in the reference state as the reference feature amount, and calculate the difference (change) between that reference feature amount and a feature amount in the feature information acquired from the extraction unit 403.

In step B5', using the calculated change information, the estimation unit 405 estimates the state of the plant by referencing the growth model, finding change information in the growth model that is similar to the calculated change information, and selecting a plant state that corresponds to the found change information.

In step B5', the following processing from (d1") to (d2") is performed.

(d1") In step B5', using the change information 181 shown in FIG. 18 that was calculated by the calculation unit 404, the estimation unit 405 references the growth model 171 shown in FIG. 17 and extracts change information that is similar to the change information 181.

(d2") Next, in step B5', the estimation unit 405 selects the "change parameter" that is associated with the extracted change information 181, and estimates the growth of the portion of the plant indicated by the "change parameter" as the plant state.

Next, in step B6', the growth information generation unit 307 generates growth information by associating the plant state estimated by the estimation unit 405 with a time that indicates the time at which the vibration information was measured.

Next, in step B7', the output information generation unit 308 then uses the growth information to generate outputtable output information in order to output the growth information to the output device 203. Thereafter, the output information generation unit 308 outputs the output information to the output device 203.

[Effects of Present Example Embodiment]

As described above, according to the present example embodiment, the use of the plant monitoring apparatus makes it possible for a user to understand the state of soil in which a plant grows and the state of the plant above the soil surface based on vibration measured via the soil and vibration produced above the target plant soil surface. In other words, the user can understand the state of the plant above the soil surface and below the soil surface.

Also, vibration that corresponds to a certain soil depth can be selected using the soil state estimation unit 200, and therefore it is possible to estimate the soil state at a target depth (soil layer) with use of vibration that corresponds to that soil layer.

Also, according to the soil state estimation unit 200, measurement such as that shown in the gain line chart of FIG. 5 is sufficient, and therefore integration can be performed with a weak continuous wave. By using the exciter 201 to intermittently or continuously apply weak vibration to the soil, it is possible to raise the SN ratio of the statistically measured vibration. For this reason, it is possible to estimate the soil state of soft soil in a field or the like without causing ridges or the like to collapse.

Furthermore, speed is not measured, and therefore a strong shock is not necessary, thus making it possible to perform measurement with the vibrometer 202 that is arranged very close to the exciter 201. In other words, with a conventional method in which hardness is measured using the transmission speed of vibration, it is necessary to detect the speed difference, that is to say the vibration transmission time difference. Also, the vibration source and the measurement location need to be separated far enough to be able to measure a time difference, and therefore strong vibration needs to be applied. However, according to the present example embodiment, there is no need to detect a speed difference, and it is sufficient to intermittently or continuously produce vibration with use of the exciter 201, measure the vibration with the vibrometer 202, and then determine the magnitude of the measured vibration, and therefore measurement can be performed with the vibrometer 202 that is arranged very close to the exciter 201.

Also, because the soil state can be estimated, outputting the soil state to the output device 203 makes it possible for a worker to take an appropriate action on the target soil layer. As one example of an appropriate action, if the soil is hard, the worker can be prompted to plow the soil, for example.

Also, by using the plant state estimation unit 300, it is possible to extract a feature amount regarding a frequency response from the vibration of a portion of a target plant (e.g., a stem, a branch, or a leaf), calculate the difference (change) between a reference feature amount and the extracted feature amount, and estimate a plant state (plant growth state) based on the calculated change of the feature amount.

According to the plant state estimation unit 300', it is possible to extract a feature amount regarding a transfer function from the vibration of a portion of a target plant, calculate the difference (change) between a reference feature amount and the extracted feature amount, and estimate the state of a fruit or the like of the plant (fruit growth state) based on the calculated change of the feature amount.

Also, with the plant state estimation units 300 and 300', even when not forcibly applying vibration that influences plant growth, it is possible to use vibration of the plant caused by minute vibration from wind, soil shift, and the like, thus making it possible to monitor the state of the plant even when vibration is not being forcibly applied. This therefore makes it possible to continuously monitor the state of the plant.

Also, because the state of the plant can be continuously monitored with the plant state estimation units 300 and 300', the growth of the plant can be easily recorded. Furthermore, the state of the plant can be continuously monitored even when a worker is at a remote location.

[Program]

It is sufficient that a program according to the example embodiment of the present invention is a program for causing a computer to execute steps A1 to A8 shown in FIG. 19, steps B1 to B7 in FIG. 20, steps C1 to C7 shown in FIG. 21, steps B1' to B7' shown in FIG. 22, and steps C1' to C7' shown in FIG. 23.

The plant monitoring apparatus and the plant monitoring method of the present example embodiment can be realized by installing the program in the computer and executing the program. In this case, the processor of the computer functions as, and performs processing as, the soil state estimation unit 200 (the control unit 204, the collection unit 205, the selection unit 206, the extraction unit 207, the estimation unit 208, and the output information generation unit 209) and the plant state estimation unit 300 (the model generation unit 302, the collection unit 303, the extraction unit 304, the calculation unit 305, the estimation unit 306, the growth information generation unit 307, and the output information generation unit 308 (209)).

Also, the program of the present example embodiment may be executed by a computer system that is constructed by multiple computers. In this case, the computers may each function as, and perform processing as, any of the soil state estimation unit 200 (the control unit 204, the collection unit 205, the selection unit 206, the extraction unit 207, the estimation unit 208, and the output information generation unit 209) and the plant state estimation unit 300 (the model generation unit 302, the collection unit 303, the extraction unit 304, the calculation unit 305, the estimation unit 306, the growth information generation unit 307, and the output information generation unit 308 (209)).

[Physical Configuration]

Figure 24:
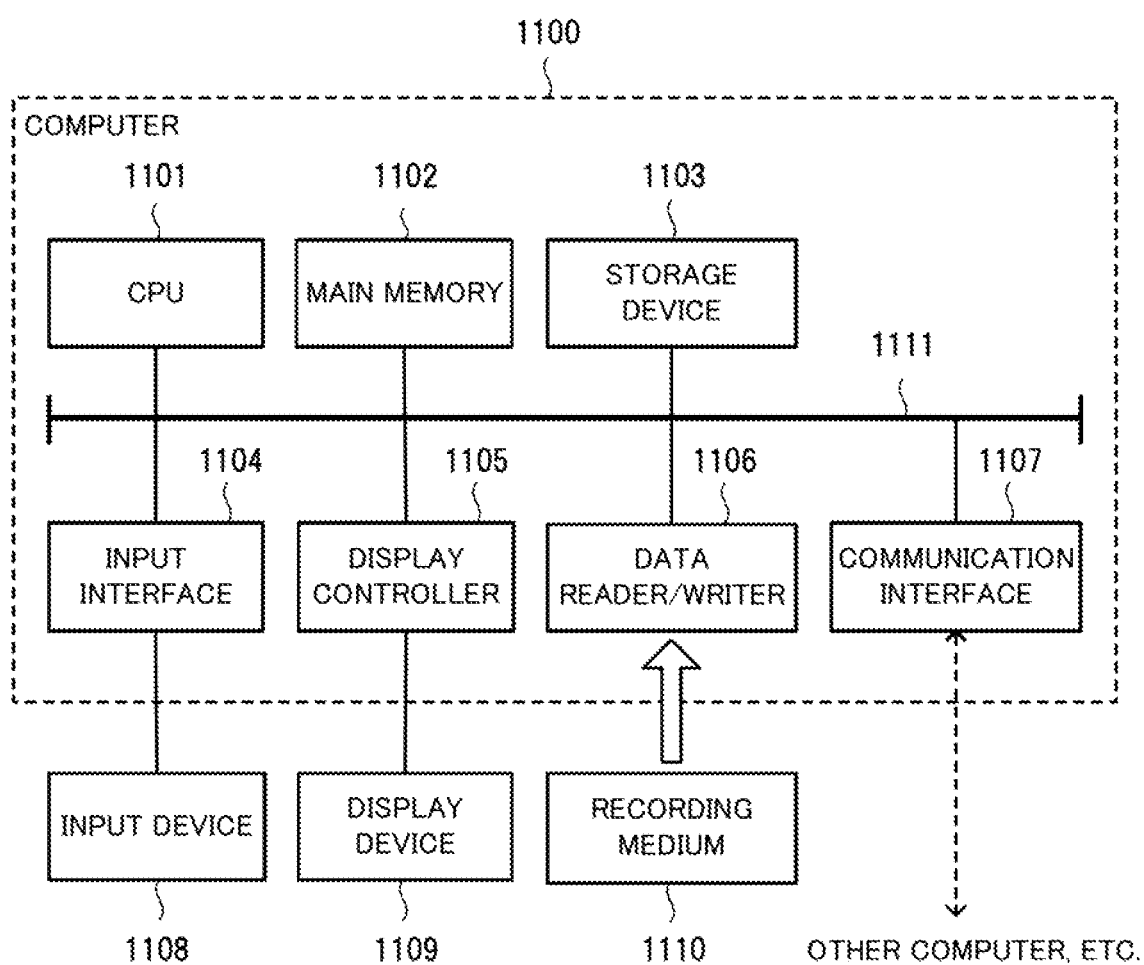
FIG. 24 is a diagram showing an example of a computer that realizes the plant monitoring apparatus.

A computer that realizes the plant monitoring apparatus by executing the program of the present example embodiment will be described below with reference to FIG. 24. FIG. 24 is a block diagram showing an example of the computer that realizes the plant monitoring apparatus according to the example embodiment of the present invention.

As shown in FIG. 24, a computer 1100 includes a CPU 1101, a main memory 1102, a storage device 1103, an input interface 1104, a display controller 1105, a data reader/writer 1106, and a communication interface 1107. These members are connected via a bus 1111 to enable the exchange of data therebetween. Note that the computer 1100 may include a GPU (Graphics Processing Unit) or an FPGA (Field-Programmable Gate Array) in addition to the CPU 1101 or instead of the CPU 1101.

The CPU 1101 carries out various types of arithmetic calculation by loading the program (code) of the present example embodiment, which is stored in the storage device 1103, to the main memory 1102 and executing portions of the program in a predetermined sequence. The main memory 1102 is typically a volatile storage device such as a DRAM (Dynamic Random Access Memory). Also, the program of the present example embodiment is provided in a state of being stored on a computer readable recording medium 1110. Note that the program of the present example embodiment may be distributed over the Internet, which can be accessed via the communication interface 1107.

Besides a hard disk drive, other examples of the storage device 1103 include a semiconductor storage device such as a flash memory. The input interface 1104 mediates the transfer of data between the CPU 1101 and input devices 1108 such as a keyboard and a mouse. The display controller 1105 is connected to a display device 1109 and controls display performed by the display device 1109.

The data reader/writer 1106 mediates the transfer of data between the CPU 1101 and the recording medium 1110, reads out the program from the recording medium 1110, and writes processing results obtained by the computer 1100 to the recording medium 1110. The communication interface 1107 mediates the transfer of data between the CPU 1101 and other computers.

Examples of the recording medium 1110 include a general-purpose semiconductor storage device such as a CF (Compact Flash (registered trademark)) or an SD (Secure Digital) card, a magnetic recording medium such as a flexible disk, and an optical recording medium such as a CD-ROM (Compact Disk Read Only Memory).

The following discloses supplementary notes regarding the example embodiments described above. The example embodiments described above can be partially or entirely realized by Supplementary Notes 1 to 18 listed below, but the present invention is not limited to the following descriptions.

(Supplementary Note 1)

A plant monitoring apparatus including:

a soil state estimating unit that estimating a state of soil by, with use of frequency association information calculated based on vibration measured via the soil, referencing soil state estimation information in which the frequency association information and information indicating states of the soil are associated with soil states; and a plant state estimating unit that estimating a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface.

(Supplementary Note 2)

The plant monitoring apparatus according to Supplementary note 1, wherein the soil state estimating unit classifies vibration measured via the soil according to soil depth with use of a transmission time for which vibration passes through the soil, and calculates the frequency association information for each vibration classification result.

(Supplementary Note 3)

The plant monitoring apparatus according to Supplementary note 2, wherein the transmission time is an amount of time from a time when vibration was applied to a target soil surface until when vibration corresponding to the applied vibration is measured at the soil surface after passing through the soil.

(Supplementary Note 4)

The plant monitoring apparatus according to Supplementary note 1, wherein the soil state estimation information is information in which soil root quantity, soil hardness, soil moisture content, soil composition, or any combination thereof is associated with the frequency association information.

(Supplementary Note 5)

The plant monitoring apparatus according to Supplementary note 1, wherein the plant state estimating unit extracts a feature amount from a frequency response of vibration of a target plant, calculates change that indicates growth of the plant based on the extracted feature amount and a reference feature amount that corresponds to a reference plant state, and uses the calculated change as the growth association information.

(Supplementary Note 6)

The plant monitoring apparatus according to Supplementary note 5, wherein the plant state estimation information is information in which a stem state, a branch state, a leaf state, a fruit state, or any combination thereof is associated with the growth association information.

(Supplementary Note 7)

A plant monitoring method including:

(a) estimating a state of soil by, with use of frequency association information calculated based on vibration measured via the soil, referencing soil state estimation information in which the frequency association information and information indicating states of the soil are associated with soil states; and (b) estimating a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface.

(Supplementary Note 8)

The plant monitoring method according to Supplementary note 7, wherein in the (a), vibration measured via the soil is classified according to soil depth with use of a transmission time for which vibration passes through the soil, and the frequency association information is calculated for each vibration classification result.

(Supplementary Note 9)

The plant monitoring method according to Supplementary note 8, wherein the transmission time is an amount of time from a time when vibration was applied to a target soil surface until when vibration corresponding to the applied vibration is measured at the soil surface after passing through the soil.

(Supplementary Note 10)

The plant monitoring method according to Supplementary note 7, wherein the soil state estimation information is information in which soil root quantity, soil hardness, soil moisture content, soil composition, or any combination thereof is associated with the frequency association information.

(Supplementary Note 11)

The plant monitoring method according to Supplementary note 7, wherein in the (b), a feature amount is extracted from a frequency response of vibration of a target plant, change that indicates growth of the plant is calculated based on the extracted feature amount and a reference feature amount that corresponds to a reference plant state, and the calculated change is used as the growth association information.

(Supplementary Note 12)

The plant monitoring method according to Supplementary note 11, wherein the plant state estimation information is information in which a stem state, a branch state, a leaf state, a fruit state, or any combination thereof is associated with the growth association information.

(Supplementary Note 13)

A non-transitory computer readable recording medium that includes a program recorded thereon, the program including instructions that causes a computer to carry out:

(a) a step of estimating a state of soil by, with use of frequency association information calculated based on vibration measured via the soil, referencing soil state estimation information in which the frequency association information and information indicating states of the soil are associated with soil states; and (b) a step of estimating a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface.

(Supplementary Note 14)

The non-transitory computer readable recording medium according to Supplementary note 13, wherein in the (a) step, vibration measured via the soil is classified according to soil depth with use of a transmission time for which vibration passes through the soil, and the frequency association information is calculated for each vibration classification result.

(Supplementary Note 15)

The non-transitory computer readable recording medium according to Supplementary note 14, wherein the transmission time is an amount of time from a time when vibration was applied to a target soil surface until when vibration corresponding to the applied vibration is measured at the soil surface after passing through the soil.

(Supplementary Note 16)

The non-transitory computer readable recording medium according to Supplementary note 13, wherein the soil state estimation information is information in which soil root quantity, soil hardness, soil moisture content, soil composition, or any combination thereof is associated with the frequency association information.

(Supplementary Note 17)

The non-transitory computer readable recording medium according to Supplementary note 13, wherein in the (b) step, a feature amount is extracted from a frequency response of vibration of a target plant, change that indicates growth of the plant is calculated based on the extracted feature amount and a reference feature amount that corresponds to a reference plant state, and the calculated change is used as the growth association information.

(Supplementary Note 18)

The non-transitory computer readable recording medium according to Supplementary note 17, wherein the plant state estimation information is information in which a stem state, a branch state, a leaf state, a fruit state, or any combination thereof is associated with the growth association information.

As described above, the present invention enables monitoring the state of a plant and the soil in which the plant grows. The present invention is applicable to fields that require the estimation of the state of a plant and the state of the soil in which the plant grows.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

What is claimed is:

1. A plant monitoring method executed by a computer, comprising:
   (a) estimating a state of soil by, with use of frequency association information calculated based on vibration measured via the soil, referencing soil state estimation information in which the frequency association information and information indicating states of the soil are associated with soil states, the soil states being a combination of soil root quantity, soil hardness, soil moisture content, and soil composition; and
   (b) estimating and outputting an indication of a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface,
   wherein estimating the state of the soil comprises controlling emission and reception of the vibration into and from the soil, and
   wherein, when the growth association information is determined to meet a predetermined condition, the indication further comprises an instruction to plow the soil.

2. The plant monitoring method according to claim 1, wherein in the (a), vibration measured via the soil is classified according to soil depth with use of a transmission time for which vibration passes through the soil, and the frequency association information is calculated for each vibration classification result.

3. The plant monitoring method according to claim 2, wherein the transmission time is an amount of time from a time when vibration was applied to a target soil surface until when vibration corresponding to the applied vibration is measured at the soil surface after passing through the soil.

4. The plant monitoring method according to claim 1, wherein in the (b), a feature amount is extracted from a frequency response of vibration of a target plant, change that indicates growth of the plant is calculated based on the extracted feature amount and a reference feature amount that corresponds to a reference plant state, and the calculated change is used as the growth association information.

5. The plant monitoring method according to claim 4, wherein the plant state estimation information is information in which a stem state, a branch state, a leaf state, a fruit state, or any combination thereof is associated with the growth association information.

6. A plant monitoring apparatus comprising:
   at least one memory configured to stores one or more instructions; and
   at least one processor configured to executes the one or more instructions to:
   estimate a state of soil by, with use of frequency association information calculated based on vibration measured via the soil, referencing soil state estimation information in which the frequency association information and information indicating states of the soil are associated with soil states, the soil states being a combination of soil root quantity, soil hardness, soil moisture content, and soil composition; and
   estimate and output an indication of a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface,
   wherein estimating the state of the soil comprises controlling emission and reception of the vibration into and from the soil, and
   wherein, when the growth association information is determined to meet a predetermined condition, the indication further comprises an instruction to plow the soil.

7. The plant monitoring apparatus according to claim 6, wherein the at least one processor is configured to:
   classify vibration measured via the soil according to soil depth with use of a transmission time for which vibration passes through the soil,
   and calculate the frequency association information for each vibration classification result.

8. The plant monitoring apparatus according to claim 7, wherein the transmission time is an amount of time from a time when vibration was applied to a target soil surface until when vibration corresponding to the applied vibration is measured at the soil surface after passing through the soil.

9. The plant monitoring apparatus according to claim 6, wherein the at least one processor is configured to:
   extract a feature amount from a frequency response of vibration of a target plant, and
   calculate change that indicates growth of the plant based on the extracted feature amount and a reference feature amount that corresponds to a reference plant state, and uses the calculated change as the growth association information.

10. The plant monitoring apparatus according to claim 9, wherein the plant state estimation information is information in which a stem state, a branch state, a leaf state, a fruit state, or any combination thereof is associated with the growth association information.

11. A non-transitory computer readable recording medium that includes a program recorded thereon, the program including instructions that causes a computer to carry out:
   (a) a step of estimating a state of soil by, with use of frequency association information calculated based on vibration measured via the soil, referencing soil state estimation information in which the frequency association information and information indicating states of the soil are associated with soil states, the soil states being a combination of soil root quantity, soil hardness, soil moisture content, and soil composition; and
   (b) a step of estimating and outputting an indication of a state of a plant by, with use of growth association information that was calculated based on vibration of the plant and indicates growth of the plant, referencing plant state estimation information in which the growth association information and information indicating states of the plant above a plant soil surface are associated with plant states above the plant soil surface, wherein estimating the state of the soil comprises controlling emission and reception of the vibration into and from the soil, and wherein, when the growth association information is determined to meet a predetermined condition, the indication further comprises an instruction to plow the soil.

12. The non-transitory computer readable recording medium according to claim 11, wherein in the (a) step, vibration measured via the soil is classified according to soil depth with use of a transmission time for which vibration passes through the soil, and the frequency association information is calculated for each vibration classification result.

13. The non-transitory computer readable recording medium according to claim 12, wherein the transmission time is an amount of time from a time when vibration was applied to a target soil surface until when vibration corresponding to the applied vibration is measured at the soil surface after passing through the soil.

14. The non-transitory computer readable recording medium according to claim 11, wherein in the (b) step, a feature amount is extracted from a frequency response of vibration of a target plant, change that indicates growth of the plant is calculated based on the extracted feature amount and a reference feature amount that corresponds to a reference plant state, and the calculated change is used as the growth association information.

15. The non-transitory computer readable recording medium according to claim 14, wherein the plant state estimation information is information in which a stem state, a branch state, a leaf state, a fruit state, or any combination thereof is associated with the growth association information.

* * * * *